US006603058B1

(12) United States Patent
Brennan et al.

(10) Patent No.: US 6,603,058 B1
(45) Date of Patent: Aug. 5, 2003

(54) NON-HUMAN ANIMAL MODEL FOR OBESITY AND USES THEREOF

(75) Inventors: Miles B. Brennan, Denver, CO (US); Ute Hochgeschwender, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/374,827

(22) Filed: Aug. 12, 1999

Related U.S. Application Data
(60) Provisional application No. 60/111,581, filed on Dec. 9, 1998, and provisional application No. 60/146,306, filed on Jul. 29, 1999.

(51) Int. Cl.[7] .................. A01K 67/00; C12N 15/00; C12Q 1/00; G01N 33/00
(52) U.S. Cl. .................. 800/18; 800/9; 800/13; 800/21; 800/22; 800/25; 800/3; 435/4
(58) Field of Search .................. 800/8, 9, 13, 21, 800/22, 25, 18, 3; 435/4

(56) References Cited

U.S. PATENT DOCUMENTS

| | | | |
|---|---|---|---|
| 4,874,744 A | 10/1989 | Norlund et al. | 514/13 |
| 4,918,055 A | 4/1990 | Hruby et al. | 514/14 |
| 5,532,347 A | 7/1996 | Cone et al. | 536/23.5 |
| 5,674,839 A | 10/1997 | Hruby et al. | 514/9 |
| 5,683,981 A | 11/1997 | Hadley et al. | 514/11 |
| 5,691,309 A | 11/1997 | Basinski et al. | 514/12 |
| 5,703,220 A | 12/1997 | Yamada et al. | 536/23.5 |
| 5,710,265 A | 1/1998 | Yamada et al. | 536/23.5 |
| 5,714,576 A | 2/1998 | Hruby et al. | 530/312 |
| 5,731,408 A | 3/1998 | Hadley et al. | 530/317 |
| 5,756,461 A | 5/1998 | Stephens | 514/12 |
| 5,766,877 A | 6/1998 | Stark et al. | 435/69.1 |
| 5,773,416 A | 6/1998 | Chehab | 514/21 |
| 5,780,258 A | 7/1998 | de la Brousse et al. | 435/29 |
| 5,786,332 A | 7/1998 | Girten et al. | 514/16 |
| 5,830,540 A | 11/1998 | Lallone | 424/85.1 |
| 5,830,994 A | 11/1998 | D'Hinterland et al. | 530/200 |
| 5,831,017 A | 11/1998 | Hoffman | 530/350 |
| 5,843,652 A | 12/1998 | Woychik | 435/6 |
| 5,846,734 A | 12/1998 | Serrero | 435/7.1 |
| 5,849,708 A | 12/1998 | Maratos-Flier | 514/13 |
| 5,851,995 A | 12/1998 | Basinski et al. | 514/12 |
| 5,866,547 A | 2/1999 | Flier et al. | 514/21 |
| 5,869,452 A | 2/1999 | Ng et al. | 514/14 |
| 5,932,779 A * | 8/1999 | Lee et al. | 800/2 |
| 6,127,381 A | 10/2000 | Basu et al. | 514/307 |

FOREIGN PATENT DOCUMENTS

WO   WO 97/47316   12/1997

OTHER PUBLICATIONS

Seamark, Progress and Emerging Problems in Livestock Transgenesis a Summary Perspective, 1994, Reprod. Fertil Dev., vol. 6, pp. 653–657.*
Plamiter et al., Metallothionein–Human GH Fusion Gene Stimulate Growth of Mice, Nov. 18, 1983, Growth of Mice–Bearing, pp. 809–814.*
Rubinstein et al., Introduction of a point mutation into the mouse genome by homologous . . . , Mar. 5, 1993, Nucleic Acid Research, vol. 21, No. 11, pp. 2613–2617.*
Wu et al., Methods in Gene Biotechnology, May 30, 1997, CRC Press, Chapter 17, pp. 339–365.*
Houdebine, Production of pharmaceutical protein from transgenic animals, 1994, Journal Biotechnology, vol. 34, pp. 269–287.*
Pursel et al., Expression and preformance in transgenic pigs, 1990, vol. 40, pp. 235–245.*
Huruby et al., Patent No. 5674839.*
AC P71236, Jun. 18, 1987, (UNIO) UCB Products SA.*
Hruby VJ,AC P82640, Nov. 23, 1988, Geneseq.*
Dores R.M. et al., AC 941589, Nov. 1, 1995, SwissProt.*
Bessesen et al., *Seminars in Oncology*, 25(2)(supp 6):28–32 (1998).
Eichhom et al., *Peptides*, 16(4):665–671 (1995).
Jordan et al., *Bioessays*, 20(8):603–606 (1998).
Mountjoy et al., *Mol. Cell. Endocrinology*, 128:171–177 (1997).
Richter et al., *Metabolism*, 34(6):539–543 (1985).
Young et al., *J. Neuroscience*, 18(17):6631–6640 (1998).
Boston et al., *Endocrinology*, 137(5):2043–2050 (1996).
Campfield et al., *Science*, 280:1383–1387 (1998).
Catania et al., *Ann. N.Y. Acad. Sci.*, 840:848–856 (1998).
Fan et al., *Nature*, 385:165–168 (1997).
Kastin et al., *Pharmacol. Biochem. Behav.*, 3(1Suppl):121–6 (1975).
König, *Peptide and Protein Hormones:Structure, Regulation, Activity; A Reference Manual*, pp. 52–82; 229–239 (Weinheim; New York; Basel; Cambridge (1993).
Krude et al., *Nature Genetics*, 19:155–157 (1998).
Rawls, *C&En*, 77(25):35–44 (1999).
Xue et al., *FASEB J.*, 12:1391–1396 (1998).
Zemel et al., *Int'l J. Obesity*, 22:678–683 (1998).
Zemel et al., *Nutr. Rev.*, 56(9):271–281 (1998).

* cited by examiner

*Primary Examiner*—Scott D. Priebe
*Assistant Examiner*—Shin-Lin Chen
(74) *Attorney, Agent, or Firm*—Brinks Hofer Gilson & Lione

(57) ABSTRACT

Described is a genetically modified non-human animal model for studying the peripheral and central pathways of energy homeostasis. Also disclosed are methods of identifying compounds for regulating such pathways and a Pomc mutant mouse.

46 Claims, 9 Drawing Sheets

FIG. 3A
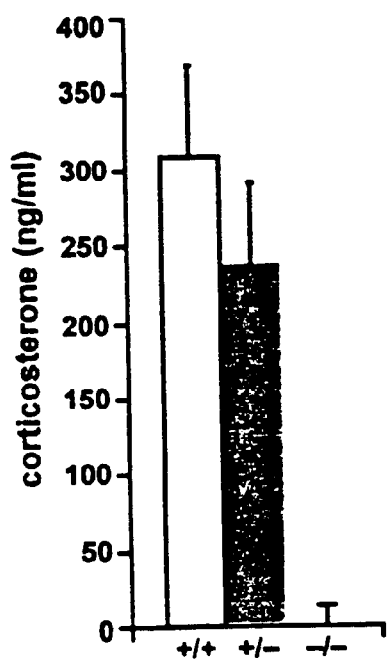
FIG. 3B
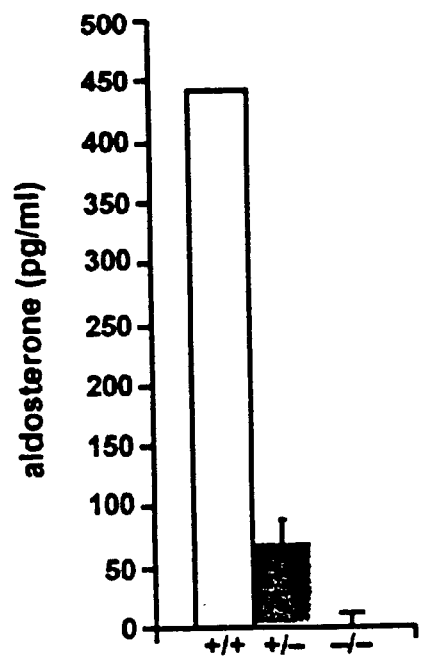
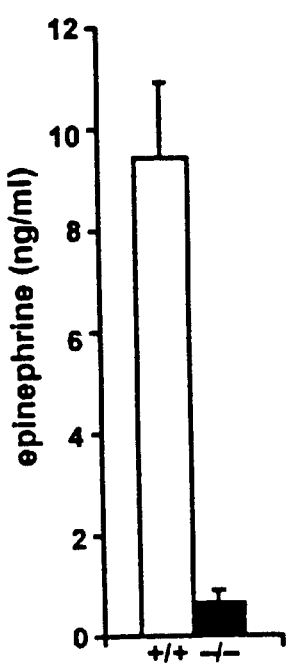
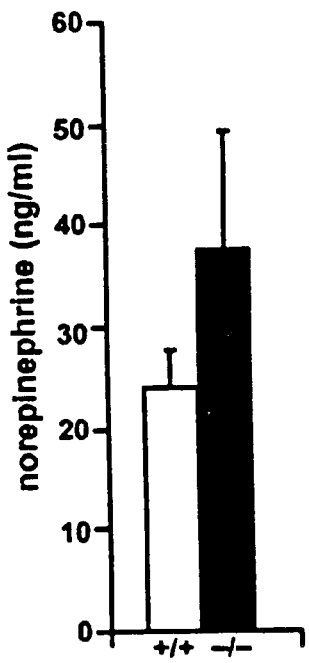
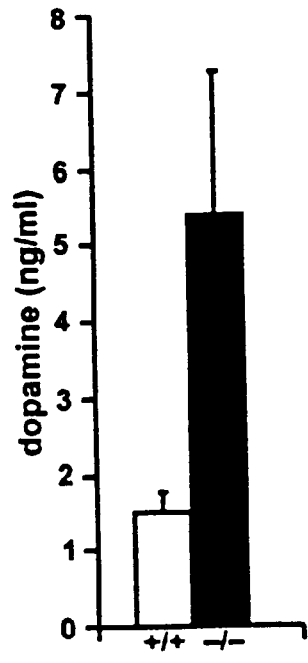
FIG. 3C    FIG. 3D    FIG. 3E FIG. 5A
FIG. 5B
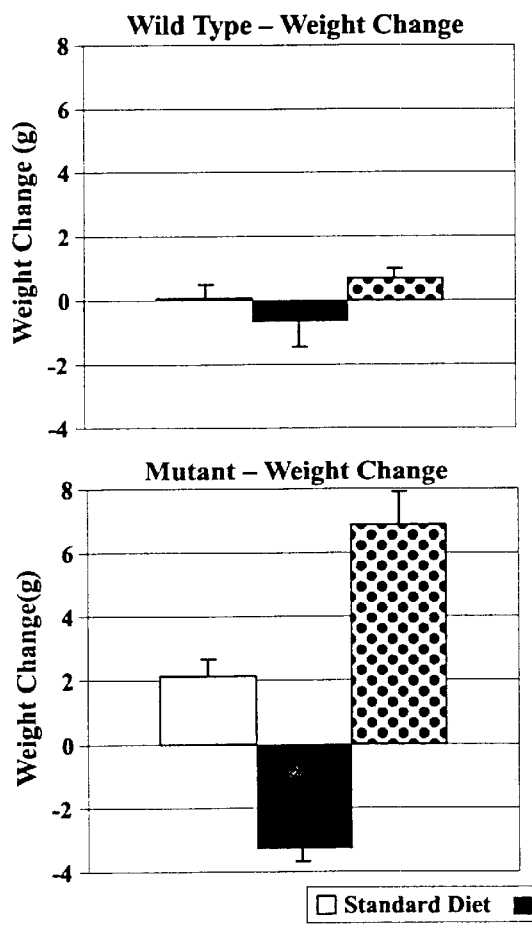
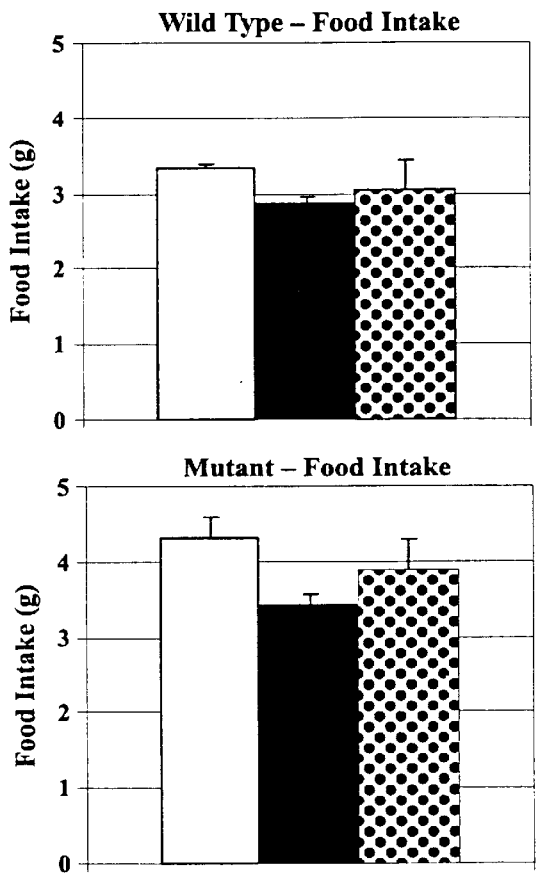
FIG. 5C
FIG. 5D

SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<221> NAME/KEY: DOMAIN
<222> LOCATION: (1)..(5)
<223> OTHER INFORMATION: conserved region

<400> SEQUENCE: 1

Glu His Phe Arg Trp

-continued

```
     1               5

<210> SEQ ID NO 2
<211> LENGTH: 13
<212> TYPE: PRT
<213> ORGANISM: Homo sapiens

<400> SEQUENCE: 2

Ser Tyr Ser Met Glu His Phe Arg Trp Gly Lys Pro Val
  1               5                  10

<210> SEQ ID NO 3
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa = Nle
<220> FEATURE:
<221> NAME/KEY: VARIANT
<222> LOCATION: (2)
<223> OTHER INFORMATION: Xaa = Glu or Asp
<220> FEATURE:
<221> NAME/KEY: VARIANT
<222> LOCATION: (4)
<223> OTHER INFORMATION: Xaa = Phe or D-Phe
<220> FEATURE:
<221> NAME/KEY: VARIANT
<222> LOCATION: (7)
<223> OTHER INFORMATION: Xaa = dibasic amino acid; Lys; Orn; Dbu; or Dpr
<220> FEATURE:
<221> NAME/KEY: PEPTIDE
<222> LOCATION: (1)..(7)
<223> OTHER INFORMATION: analog

<400> SEQUENCE: 3

Xaa Xaa His Xaa Arg Trp Xaa
  1               5

<210> SEQ ID NO 4
<211> LENGTH: 13
<212> TYPE: PRT
<213> ORGANISM: Artificial Sequence
<220> FEATURE:
<221> NAME/KEY: VARIANT
<222> LOCATION: (4)
<223> OTHER INFORMATION: Xaa = Met, Nle, or Cys
<220> FEATURE:
<221> NAME/KEY: MOD_RES
<222> LOCATION: (7)
<223> OTHER INFORMATION: Phe = D-Phe
<220> FEATURE:
<221> NAME/KEY: PEPTIDE
<222> LOCATION: (1)..(13)
<223> OTHER INFORMATION: analog

<400> SEQUENCE: 4

Ser Tyr Ser Xaa Glu His Phe Arg Trp Gly Lys Pro Val
  1               5                  10

<210> SEQ ID NO 5
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: Nle
<220> FEATURE:
<221> NAME/KEY: MOD_RES
<222> LOCATION: (4)
```

```
<223> OTHER INFORMATION: Xaa = D-naphthylalanine
<220> FEATURE:
<221> NAME/KEY: PEPTIDE
<222> LOCATION: (1)..(7)
<223> OTHER INFORMATION: analog

<400> SEQUENCE: 5

Xaa Asp His Xaa Arg Trp Lys
 1               5

<210> SEQ ID NO 6
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa = Nle
<220> FEATURE:
<221> NAME/KEY: MOD_RES
<222> LOCATION: (4)
<223> OTHER INFORMATION: Phe = D-para-iodo-phenylalanine
<220> FEATURE:
<221> NAME/KEY: PEPTIDE
<222> LOCATION: (1)..(7)
<223> OTHER INFORMATION: analog

<400> SEQUENCE: 6

Xaa Asp His Phe Arg Trp Lys
 1               5

<210> SEQ ID NO 7
<211> LENGTH: 845
<212> TYPE: DNA
<213> ORGANISM: Mus musculus

<400> SEQUENCE: 7
gccaggcttg gctcactcgc ctggcctccc tacaggcttg catccgggct tgcaaactcg      60
acctctcgct ggagacgccc gtgtttcctg gcaacggaga tgaacagccc ctgactgaaa     120 accccggaa gtacgtcatg ggtcacttcc gctgggaccg cttcggcccc aggaacagca     180
gcagtgctgg cagcgcggcg cagaggcgtg cggaggaaga ggcggtgtgg ggagatggca     240
gtccagagcc gagtccacgc gagggcaagc gctcctactc catggagcac ttccgctggg     300
gcaagccggt gggcaagaaa cggcgcccgg tgaaggtgta ccccaacgtt gctgagaacg     360
agtcggcgga ggccttttcc ctagagttca gagggagct ggaaggcgag cggccattag     420
gcttggagca ggtcctggag tccgacgcgg agaaggacga cgggccctac cgggtggagc     480
acttccgctg gagcaacccg cccaaggaca agcgttacgg tggcttcatg acctccgaga     540
agagccagac gcccctggtg acgctcttca agaacgccat catcaagaac gcgcacaaga     600
agggccagtg agggtgcagg ggtcttctca ttccaaggcc ccctccctgc atgggcgagc     660
tgatgacctc tagcctctta gagttacctg tgttaggaaa taaaacctt cagatttcac     720 agtcggctct gatcttcaat aaaaactgcg taaataaagt caaaacacaa ctgtccagtt     780
acactatcac gtgaccagat gctagaatgt aaagaaaaca tttctcaacc tccttgcccc     840
agcaa                                                                  845

<210> SEQ ID NO 8
<211> LENGTH: 235
<212> TYPE: PRT
<213> ORGANISM: Mus musculus

<400> SEQUENCE: 8
```

-continued

```
Met Pro Arg Phe Cys Tyr Ser Arg Ser Gly Ala Leu Leu Leu Ala Leu
 1           5                  10                      15

Leu Leu Gln Thr Ser Ile Asp Val Trp Ser Trp Cys Leu Glu Ser Ser
            20                  25                  30

Gln Cys Gln Asp Leu Thr Thr Glu Ser Asn Leu Leu Ala Cys Ile Arg
         35                  40                      45

Ala Cys Lys Leu Asp Leu Ser Leu Glu Thr Pro Val Phe Pro Gly Asn
     50                  55                  60

Gly Asp Glu Gln Pro Leu Thr Glu Asn Pro Arg Lys Tyr Val Met Gly
 65                  70                  75                  80

His Phe Arg Trp Asp Arg Phe Gly Pro Arg Asn Ser Ser Ser Ala Gly
             85                  90                  95

Ser Ala Ala Gln Arg Arg Ala Glu Glu Glu Ala Val Trp Gly Asp Gly
            100                 105                 110

Ser Pro Glu Pro Ser Pro Arg Glu Gly Lys Arg Ser Tyr Ser Met Glu
            115                 120                 125

His Phe Arg Trp Gly Lys Pro Val Gly Lys Lys Arg Arg Pro Val Lys
            130                 135                 140

Val Tyr Pro Asn Val Ala Glu Asn Glu Ser Ala Glu Ala Phe Pro Leu
145                 150                 155                 160

Glu Phe Lys Arg Glu Leu Glu Gly Glu Arg Pro Leu Gly Leu Glu Gln
                165                 170                 175

Val Leu Glu Ser Asp Ala Glu Lys Asp Asp Gly Pro Tyr Arg Val Glu
            180                 185                 190

His Phe Arg Trp Ser Asn Pro Pro Lys Asp Lys Arg Tyr Gly Gly Phe
            195                 200                 205

Met Thr Ser Glu Lys Ser Gln Thr Pro Leu Val Thr Leu Phe Lys Asn
    210                 215                 220

Ala Ile Ile Lys Asn Ala His Lys Lys Gly Gln
225                 230                 235
```

NON-HUMAN ANIMAL MODEL FOR OBESITY AND USES THEREOF

CROSS-REFERENCE TO RELATED APPLICATIONS

This invention claims priority under 35 U.S.C. § 119(e) from U.S. Provisional Application Serial No. 60/111,581, filed Dec. 9, 1998, entitled, "Composition and Method for Controlling Obesity", and from U.S. Provisional Application Serial No. 60/146,306, filed Jul. 29, 1999, entitled "Composition and Method for Controlling Body Weight and Conditions Related Thereto". The entire disclosures of U.S. Provisional Application Serial No. 60/111,581 and U.S. Provisional Application Serial No. 60/146,306 are incorporated herein by reference.

FIELD OF THE INVENTION

The present invention relates to a non-human animal model for obesity and uses of such an animal for studying and developing methods for modifying the peripheral as well as the central melanocortinergic pathways towards controlling body weight. In particular, the present invention relates to a proopiomelanocortin (Pomc) homozygous mutant mouse and uses thereof.

BACKGROUND OF THE INVENTION

The regulation of body weight, and particularly, obesity and conditions related thereto, is a major health concern throughout the world, and particularly in the United States, contributing to morbidity and mortality. Obesity is a metabolic disorder characterized by excessive accumulation of fat stores in adipose tissue. In humans, its causes are a complex interplay of genetics, environment and culture. It is well known that a regimen of diet and exercise leading to weight loss is the best approach for treating obesity, but unfortunately, such regimens are frequently unsuccessful. Oftentimes, an individual's inability to lose weight may be due to genetically inherited factors that contribute to increased appetite, a preference for high calorie foods, reduced physical activity and an abnormal metabolism. People inheriting or acquiring such predispositions are prone to obesity regardless of their efforts to combat the condition.

On the other side of the spectrum of body weight problems, other individuals suffer from one or more "wasting" disorders (e.g., wasting syndrome, cachexia, sarcopenia) which cause undesirable and/or unhealthy loss of weight or loss of body cell mass. In the elderly as well as in AIDS and cancer patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, extraintestinal Crohn's disease, psychogenic disease, chronic heart failure or other severe trauma, frequently suffer from wasting disease which is sometimes also referred to as cachexia, ametabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, 1999, *J. Nutr.* 129(1S Suppl.): 256S-259S). Sarcopenia, yet another such disorder which can affect the aging individual, is typically characterized by loss of muscle mass. End stage wasting disease as described above can develop in individuals suffering from either cachexia or sarcopenia.

In addition to the obvious health risks associated with being overweight or underweight, the tangential detrimental effects of such conditions are equally troublesome. For the obese individual, health effects can include a myriad of physical conditions related to, or affected by, excess body weight (e.g., cardiovascular disease, diabetes, cancer, hypertension, etc.) as well as physiological damage due to an overweight person's loss of self-esteem, depression, etc. For the underweight individual, conditions related to or affected by low body weight can include heart failure, susceptibility to infectious disease as a result of immune system weakness, and depression. Moreover, the rise in bulemia and anorexia in the past few decades is alarming, and illustrates the disturbing emphasis on ideal body size and shape regardless of the severe health consequences.

Radical treatments to treat obesity include surgical procedures such as liposuction and stomach stapling. In addition, numerous drugs have been utilized in an effort to regulate a person's metabolism and/or to decrease appetite. Many of such drugs, however, have demonstrated harmful effects and have since been taken off of the market. Other replacement drug therapies have proven less effective, and the long term health consequences of such drugs are unknown. For the underweight individual, who may be suffering from undesired weight loss due to a disease such as cancer or AIDS, efforts to maintain or gain weight can be equally problematic.

Faced with such a long felt, but unsolved need for simple and effective methods for regulating body weight, researchers, over the last several decades, have expended literally hundreds of millions of dollars to investigate compounds that can be used to treat body weight problems such as obesity without the negative implications experienced with other, previously tested, weight regulating drugs. While altering appetite can affect weight, so can the regulation of the fat stores in adipose tissue. This latter approach has been an under-appreciated field relative to regulation of appetite. For instance, compared to the list of compounds directed at inhibition of energy uptake (appetite suppressants), very few compounds have been identified which stimulate fat mobilization or suppress lipid sequestration.

Physiologists have postulated for years that, when a mammal overeats, the resulting excess fat stores signal to the brain that the body is obese which, in turn, causes the body to eat less and burn more dietary fat. G. R. Hervey, *Nature* (London), 227:629–631 (1969). This model of feedback inhibition is supported by parabiotic experiments, which implicates circulating hormones controlling adiposity. Genetic studies in model organisms, especially the mouse, have allowed the identification of molecules important for the regulation of body weight. These include leptin (Zhang et al., 1995, *Nature* 372:425–432, incorporated herein by reference in its entirety), a leptin receptor (Tartaglia et al., 1995, *Cell* 83:1263–1271) and a melanocortin receptor (Huszar et al., 1997, *Cell* 88:131–141).

Findings from several lines of investigations have placed proopiomelanocortin (Pomc) and the peptides derived from it at a pivotal position in the central pathways for energy homeostasis. Obesity in the autosomal dominant lethal yellow ($A^y/a$) mouse, for example, is caused by ectopic expression of the agouti protein in the brain, where it antagonizes the melanocortin receptor 4 (MC4-R), a receptor found within the central nervous system (Lu et al., 1994, *Nature* 371:799–802). Agouti-related protein (AgRP) is normally expressed in the brain and antagonizes MC4-R. In transgenic mice, overexpression of AgRP results in obesity (Graham et al, 1997, *Nat. Genet.* 17:273–274 and Ollmann et al., 1997, *Science* 278:135–138). Targeted deletion of the MC4-R produces obesity similar to that of A$^y$ mice, which is characterized by adult onset obesity and increased linear growth (Huszar et al., 1997, *Cell* 88:131–141). Pharmacological evidence has further suggested the importance of a melanocortinergic pathway in the central regulation of energy balance: decreased feeding was observed after central administration of an MC4-R agonist (α-MSH analog) to normal mice and increased feeding after central administration of a synthetic MC4-R antagonist to normal mice when measured for 12 hours (Fan et al., 1997, *Nature* 385:165–168).

Understanding of the regulation of fat stores was greatly advanced by the discovery of leptin, the gene affected in the obese (ob) mutation. Leptin is secreted by adipose tissue, and its levels increase with increasing fat stores. Leptin is known to have both central and peripheral effects. There are high affinity receptors for leptin in the hypothalamus. Absence of either leptin or the leptin receptor leads to morbid obesity, presumably because the hypothalamus receives no fat signal, and accordingly acts as if the animal is completely without fat stores, and in some manner directs adipocytes to accumulate fat. The use of leptin to treat obesity in mice, however, requires very high, non-physiological doses. Thus, leptin alone has not been found to be a particularly useful anti-obesity agent.

To treat wasting and cachexia in patients such as the elderly, AIDS patients and cancer patients, anabolic steroids, growth hormone, dietary regimens, erythropoietin, cytokine therapy and anti-cytokine therapy, among other therapies, have been used to try to improve the condition of such patients. Such therapies cross a wide range of target cells, may have undesirable systemic side effects, may require toxic doses to work, and may not be sufficient to completely address the complex biological dysfunction related to different types of wasting disorders, however, and therefore, research is ongoing in the effort to find additional solutions to this problem.

Therefore, there remains a need in the art for a simple, safe and effective method for controlling body weight and for treating conditions related to or caused by undesired, health-compromising body weight.

The development of transgenic and "knock-out" animal technology has provided significant advances for obtaining more complete information about complex systems in vivo. By manipulating the expression of gene(s) in vivo, it is possible to gain insight into the roles of such genes in a particular system or to study aspects of the system in a genetically controlled environment. The biochemical activities associated with obesity in a small mammal such as the mouse, will allow analysis of the disorder, and conditions related thereto, at molecular and cellular levels that are often impossible to analyze in humans.

SUMMARY OF THE INVENTION

The present invention generally relates to a non-human animal model for studying and developing protocols for modifying the peripheral as well as the central melanocortinergic pathways controlling body weight. In particular, the present invention relates to a genetically modified non-human animal comprising a genetic modification within at least one allele of its Pomc locus, wherein the genetic modification results in a reduction in proopiomelanocortin (Pomc) peptide action in the animal. In one embodiment, the present invention relates to a POMC homozygous mutant mouse model. Such animal models are used for studying and developing protocols for modifying the peripheral as well as the central melanocortinergic pathways controlling body weight in Pomc mutants, for studying and developing protocols for controlling other forms of weight dysregulation, and for determining which of the specific POMC compounds are most efficient at mediating the effects on weight loss or weight gain and on adrenal insufficiency.

More particularly, one embodiment of the present invention relates to a genetically modified non-human animal useful for studying peripheral and central pathways of energy homeostasis. The genetically modified non-human animal comprises a genetic modification within at least one allele of its Pomc locus, wherein the genetic modification results in a reduction in proopiomelanocortin (Pomc) peptide action in the animal (e.g., a heterozygous mutant animal). In one embodiment, the genetic modification includes, but is not limited to, a deletion, an insertion, a substitution and/or an inversion of nucleotides in the Pomc locus. The genetic modification can be a modification including or within exon 3 of the Pomc locus which results in a reduction in Pomc peptide action, or a modification in a region of the Pomc locus other than exon 3 which results in a reduction in Pomc peptide action (e.g., exon 1, exon 2 and/or a regulatory region of the Pomc locus). In a preferred embodiment, the genetic modification is a deletion of a nucleic acid sequence within at least one allele of the Pomc locus, wherein the deletion results in an reduction of expression of Pomc peptides by the animal. In another embodiment, the animal comprises a genetic modification within two alleles (i.e., both alleles) of the Pomc locus, wherein the genetic modification results in an absence of Pomc peptide action in the animal (e.g., a homozygous mutant animal). Preferably, the genetic modification is a deletion of a nucleic acid sequence within both alleles of the Pomc locus, wherein the deletion results in an absence of expression of Pomc peptides by the animal.

In one embodiment of the present invention, the genetic modification is a deletion of a nucleic acid sequence comprising exon 3 of Pomc. In another embodiment, the genetic modification is a deletion of exon 3 of Pomc. In yet another embodiment, the genetic modification is a deletion of a portion of exon 3 of Pomc sufficient to reduce or prevent expression of Pomc peptides by at least one allele and more preferably, by both alleles, of the Pomc locus of the animal. In further embodiments of the present invention, the genetically modified non-human animal is characterized by a phenotypic characteristic which includes, but is not limited to obesity, a defect in adrenal development, altered pigmentation, measurably increased serum leptin levels, increased food uptake, and/or measurably reduced serum levels of a hormone selected from the group of corticosterone, aldosterone and epinephrine, as compared to a wild-type sibling of the animal.

In one embodiment of the present invention, the genetically modified non-human animal is a mouse. In this embodiment, the genetic modification is preferably a deletion from the genome of a nucleic acid sequence comprising SEQ ID NO:7, although other modifications as discussed above, which result in a reduction in the action of Pomc peptides, are encompassed by the present invention.

Another embodiment of the present invention relates to a method to study the molecular and biochemical events associated with body weight gain and loss, and particularly, with such events that are associated with obesity. More particularly, such a method includes the steps of: (a) harvesting cells, tissues or body fluids from a genetically modified non-human animal of the present invention; and, (b) comparing the cells, tissues or body fluids from the genetically modified non-human animal to cells, tissues or body fluids from a wild-type sibling of the genetically modified non-human animal. In one embodiment, the step of comparing is performed by an assay selected from the group consisting of morphological examination of the cells, tissues or body fluids; histological examination of the cells, tissues or body fluids; evaluation of Pomc peptide biological activity in the animal; evaluation of free fatty acid metabolism in the animal; evaluation of lipolysis and fatty acid sequestration in the animal; evaluation of weight gain or loss in the animal; evaluation of hormone levels in the animal; and, evaluation of blood biochemistry in the animal.

Yet another embodiment of the present invention relates to a method to identify POMC compounds, and particularly, homologues and mimetics, for use in regulating peripheral and central pathways of energy homeostasis. The method includes the steps of: (a) administering a compound to be evaluated to a genetically modified non-human animal which comprises a genetic modification within two (both) alleles of its Pomc locus, wherein the genetic modification results in an absence of Pomc peptide action in the animal; and, (b) evaluating physiological and pathological changes in the genetically modified non-human animal as compared to a non-human animal selected from the group of: (i) a second genetically modified non-human animal comprising a genetic modification within at least one allele of its pomc1 locus, wherein the genetic modification results in a reduction in proopiomelanocortin (Pomc) peptide action in the animal; and (ii) a third non-human animal having a genome comprising a wild-type pomc1 locus at two (i.e., both) alleles. Various compounds which can be evaluated include, but are not limited to POMC compounds, including a Pomc peptide (i.e., a peptide encoded by the Pomc gene), a fragment of such a peptide (including both biologically active and inactive fragments), a homologue of such a peptide, a mimetic (peptide or non-peptide) of such a peptide, a fusion protein comprising such a peptide, and any pharmaceutical salts of such a peptide, as well as any non-Pomc peptide.

Yet another embodiment of the present invention relates to a method of producing a genetically modified non-human animal useful for studying peripheral and central pathways of energy homeostasis. Such a method includes the steps of: (a) introducing into an embryonic stem cell of a non-human animal a targeting vector comprising a Pomc locus containing a modification of a nucleic acid sequence sufficient to result in a reduction in proopiomelanocortin (Pomc) peptide action in the animal; and, (b) obtaining progeny having the modification stably incorporated into their genome, wherein the modification results in a reduction in expression of proopiomelanocortin (Pomc) peptides by the animal. In one embodiment, this method additionally includes the step of obtaining progeny having the modification stably incorporated into their genome, wherein the modification results in an absence of expression of Pomc peptides by the animal. In a preferred embodiment, the modification is a deletion in a nucleic acid sequence sufficient to result in the reduction of Pomc peptide action in the animal.

Another embodiment of the present invention is a genetically modified mouse useful for studying peripheral and central pathways of energy homeostasis. The mouse is produced by a method comprising the steps of: (a) isolating from a source of murine genomic DNA a nucleic acid molecule comprising SEQ ID NO:7; (b) modifying a nucleic acid sequence comprising SEQ ID NO:7 in the nucleic acid molecule to form a genetically modified nucleic acid molecule; (c) inserting a selectable marker into the genetically modified nucleic acid molecule to create a targeting vector; (d) transfecting the targeting vector into embryonic stem cells; (e) selecting embryonic stem cells from step (d) which have incorporated the targeting vector at a target locus comprising SEQ ID NO:7 by homologous recombination; (f) inserting the embryonic stem cells comprising the targeting vector into non-human animal blastocysts; and, (g) impregnating a female surrogate with the non-human animal blastocysts to produce the genetically modified mouse. In a preferred embodiment, the modification of step (b) is a deletion in the nucleic acid sequence comprising SEQ ID NO:7.

BRIEF DESCRIPTION OF THE DRAWINGS OF THE INVENTION

FIG. 3A is a bar graph showing that corticosterone levels in mutant POMC mice were below the detection limit of the RIA.

FIG. 3B is a bar graph showing that aldosterone levels in mutant POMC mice were below the detection limit of the RIA.

FIG. 3C is a bar graph showing that epinephrine levels were significantly lower in mutant POMC mice as compared to wildtype mice.

FIG. 3D is a bar graph showing that norepinephrine levels were not significantly different in mutant POMC mice as compared to wildtype mice.

FIG. 3E is a bar graph showing that dopamine levels were slightly increased in mutant POMC mice as compared to wildtype mice.

FIG. 5A is a bar graph illustrating body weight change in wildtype mice under conditions of standard diet, standard diet and α-MSH analog treatment, or high fat diet.

FIG. 5B is a bar graph illustrating food intake in wildtype mice under conditions of standard diet, standard diet and α-MSH analog treatment, or high fat diet.

FIG. 5C is a bar graph illustrating body weight change in Pomc mutant mice under conditions of standard diet, standard diet and α-MSH analog treatment, or high fat diet.

FIG. 5D is a bar graph illustrating food intake in Pomc mutant mice under conditions of standard diet, standard diet and α-MSH analog treatment, or high fat diet.

DETAILED DESCRIPTION OF THE INVENTION

Figures 1A, 1B, 1C:
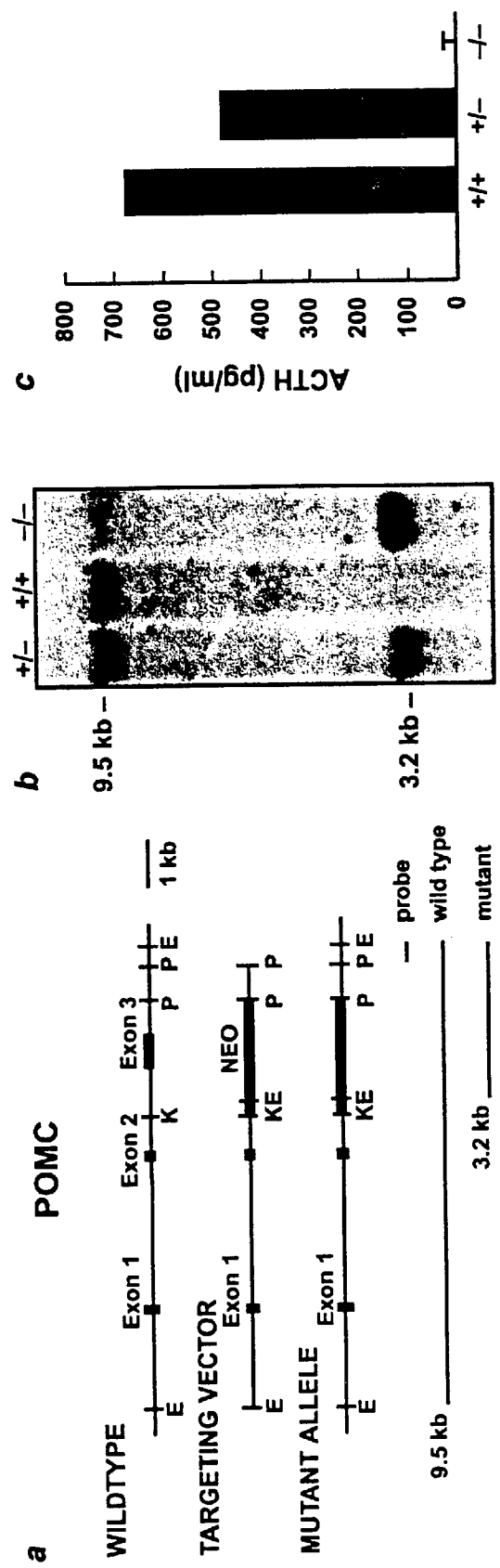
FIG. 1A is a schematic diagrams and restriction map of the mouse Pomc locus, the targeting vector, and the predicted structure of the Pomc locus after homologous recombination.
FIG. 1B is a scanned image of a Southern blot analysis of tail DNAs from $F_2$ littermates.
FIG. 1C is a bar graph showing an RIA analysis of serum ACTH levels in $F_2$ male littermates.

The present invention generally relates to a non-human animal model for studying and developing protocols for modifying the peripheral as well as the central melanocortinergic pathways controlling body weight. In particular, the present invention relates to a genetically modified non-human animal which has a genetic modification that results in a reduction, and preferably absence, of proopiomelanocortin (Pomc) peptide action in the animal, and the use of such an animal for studying and developing protocols for controlling body weight and health-compromising conditions related thereto.

More particularly, the present inventors disclose herein the development and characterization of a Pomc mutant mouse which is a model of obesity, and which can be used to study and develop protocols for the treatment of a variety of conditions related to undesirable and/or medically unhealthy body weight. The Pomc mutant mouse was engineered to carry an autosomal recessive null allele of the Pomc gene (i.e., pomc). This mouse lacks all of the peptide hormones encoded by the Pomc locus. The present inventors have discovered that mice lacking the Pomc peptides have obesity, a defect in adrenal development, and altered pigmentation. This phenotype is similar to the recently identified human Pomc mutants (Krude, et al., 1998, *Nat Genet* 19, 155–7). In addition to a dysregulation of fat metabolism, the POMC-deficient mice showed increased food intake.

When the inventors treated the mutant mice peripherally with a stable α-MSH agonist, these mice lost over 40% of their excess weight after two weeks, whereas wildtype non-obese mice did not lose significant weight. The present inventors have shown that the weight changes in POMC null mice are not simply regulated through feeding behavior, but rather through both central and peripheral actions of melanocortins. Based on in vivo experiments described herein, the present inventors have shown MSH to be an adiposity regulating hormone. Most importantly, peripheral treatment of pomc/pomc mutants with an MSH mimetic ameliorated obesity, but did not significantly diminish weight in normal mice. Consequently, these results indicate that certain subpopulations of obese patients will be particularly amenable to treatment with MSH and homologues and mimetics thereof, although the present invention indicates that the use of POMC compounds to treat any patient with undesired body weight is feasible. Pharmacological agents which are biologically active and mimic the activity of MSH are therefore useful for treating obese patients, particularly those with abnormal levels of circulating MSH. The present inventors are the first to appreciate that the Pomc peptides have both a central and peripheral effect on feeding behavior and in body weight regulation.

Furthermore, the present inventors have demonstrated that the POMC null mutant mouse is a model for studying the human POMC null syndrome. In addition to having a mouse model for the human POMC deficiency, the Pomc mutant mouse is a valuable addition to the growing number of murine obesity models, aiding in the dissection of the mechanisms of energy homeostasis, centrally and peripherally, as well as in exploring therapeutic regimens for the human POMC deficient patients and possibly for other, multigenic-multifactorial forms of human obesity. The anti-obesity effects of MSH indicate a therapeutic use in POMC-deficient as well as other forms of obesity.

The discovery by the present inventors is particularly significant, because, prior to the present invention, findings from several lines of investigations have placed proopiomelanocortin (Pomc) and the peptides derived from it at a pivotal position in the central pathways for energy homeostasis (Lu et al., 1994, supra, Graham et al., 1997, supra, Ollmann et al., 1997, supra, Huzar et al., 1997, supra, Fan et al., 1997, supra). While other investigators have focused on this recognition that proopiomelanocortins (Pomc) are involved in the central pathways for energy homeostasis, however, the present inventors, through the development and study of mice with a targeted deletion of the Pomc gene, were the first to appreciate the role of Pomc peptides in the regulation of peripheral pathways of energy homeostasis (i.e., adipocyte regulation through inhibition of free fatty acid uptake and/or stimulation of lipolysis).

One embodiment of the present invention relates to a genetically modified non-human animal useful for studying peripheral and central pathways of energy homeostasis.

The genetically modified non-human animal comprises a genetic modification within at least one allele of its Pomc locus, wherein the genetic modification results in a reduction in proopiomelanocortin (Pomc) peptide action in the animal (e.g., a heterozygous mutant animal). In one embodiment, the genetic modification includes, but is not limited to, a deletion, an insertion, a substitution and/or an inversion of nucleotides in the Pomc locus which result in a reduction in Pomc peptide action in the animal. The genetic modification can be a modification including or within exon 3 of the Pomc locus which results in a reduction in Pomc peptide action, and/or a modification in a region of the Pomc locus other than exon 3 which results in a reduction in Pomc peptide action (e.g., exon 1, exon 2 and/or a regulatory region of the Pomc locus). In a preferred embodiment, the genetic modification is a deletion of a nucleic acid sequence within at least one allele of the Pomc locus, wherein the deletion results in an reduction of expression of Pomc peptides by said animal. In another embodiment, the animal comprises a genetic modification within two alleles (i.e., both alleles) of the Pomc locus, wherein the genetic modification results in an absence of Pomc peptide action in the animal (e.g., a homozygous mutant animal). Preferably, the genetic modification is a deletion of a nucleic acid sequence within both alleles of the Pomc locus, wherein the deletion results in an absence of expression of Pomc peptides by the animal.

Proopiomelanocortin (Pomc) peptides, including the melanocortins: adrenocorticotrophin (ACTH); α-, β- and γ-melanocyte stimulating hormones (MSH); and the opioid receptor ligand β-endorphin, have a diverse array of biological activities, including roles in pigmentation, adrenocortical function, regulation of energy stores, and the immune, central nervous and peripheral circulation system (Smith, A.I. et al., *Endocr Rev* 9, 159–179 (1988); König, "Peptide and protein hormones: structure, regulation, activity, a reference manual" (Weinheim; N.Y. 1993)). As used herein, reference to Pomc peptides is intended to refer generically to any one or more of the Pomc peptides encoded by the Pomc locus. If reference to a specific Pomc peptide, such as MSH, is intended, the name of the specific peptide will be used. The nucleic acid and amino acid sequences for the naturally occurring Pomc peptides in a large variety of animals (i.e., human, mouse, rat, rabbit, bovine, ovine, macaque, amphibian, etc.) are known in the art. Such sequences can be found, for example, in a protein or nucleic acid database such as GenBank. GenBank accession numbers for such Pomc peptide (i.e., amino acid) sequences include, but are not limited to: Accession Nos. NP_000930 or CAA24754 (Homo sapiens); Accession No. P06297 (rabbit); Accession No. P01194 (rat); Accession No. P01193 (mouse); Accession No. P01191 (sheep); and, Accession No. P01190 (bovine). GenBank accession numbers for such Pomc nucleic acid sequences include, but are not limited to: Accession No. NM_000939 (Homo sapiens); Accession No. AH005319 (mouse); Accession Nos. J00016, J00019, J00021 (bovine); Accession No. S73519 (swine); S57982 (ovine); and Accession No. AH002232 (rat). Exons 1, 2 and 3 for the mouse Pomc locus are identified as GenBank Accession Nos. J00610, J00611 and J00612, respectively.

As used herein, a non-human animal suitable for genetic modification according to the present invention is any non-human animal for which the Pomc locus can be manipulated, including non-human members of the Vertebrate class, Mammalia, such as non-human primates and rodents. Preferably, such a non-human animal is a rodent, and more preferably, a mouse. Genetically modified mice which have either a reduction or an absence of Pomc peptide expression are described in detail in the Examples section.

According to the present invention, a "genetically modified" animal, such as any of the preferred non-human animals described herein, has a genome which is modified (i.e., mutated or changed) from its normal (i.e., wild-type or naturally occurring) form such that the desired result is achieved (e.g., a reduction in the action of Pomc peptides). Genetic modification of an animal is typically accomplished using molecular genetic and cellular techniques, including manipulation of embryonic cells and DNA (e.g., DNA comprising the Pomc locus). Such techniques are generally disclosed for mice, for example, in "Manipulating the Mouse Embryo" (Hogan et al., Cold Spring Harbor Laboratory Press, 1994, incorporated herein by reference in its entirety). Additionally, techniques for genetic modification of a mouse through molecular technology are described in detail in the Examples section.

A genetically modified non-human animal can include a non-human animal in which nucleic acid molecules have been modified (i.e., mutated; e.g., by insertion, deletion, substitution, and/or inversion of nucleotides), in such a manner that such modifications provide the desired effect within the animal (i.e., reduction in Pomc peptide action). As used herein, genetic modifications which result in a reduction in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of: a partial or complete deletion of the gene or of an exon within the gene (i.e., the gene does not exist, and therefore the protein can not be produced); a mutation (e.g., a deletion, substitution, insertion and/or inversion) in the gene which results in incomplete or no translation of the protein (e.g., a mutation which causes a frame shift so that the correct protein is not expressed, a mutation in one or more exons of the gene so that the protein or at least a portion of the protein is not expressed, or a mutation in a regulatory region so that the protein is not expressed or has reduced expression); or a mutation in the gene which decreases or abolishes the natural function of the protein (e.g., a protein is expressed which has decreased or no biological activity or action).

According to the present invention, a genetic modification of a non-human animal results in a reduction (i.e., decrease, inhibition, down-regulation) of the action of Pomc peptides. Such a genetic modification includes any type of modification to a genome of the animal, particularly including modifications made at the embryonic stage of development of the animal (or in the ancestor of the animal). Such modifications are described above. According to the present invention, reference to reducing "the action" (or activity) of Pomc peptides refers to any genetic modification in the non-human animal which results in decreased functionality of one or more of the Pomc peptides, including: reduced biological activity of the peptides (e.g., reduced in vivo hormonal activity); inhibition or degradation of the peptides (i.e., the peptides are expressed, but are inhibited or degraded as a result of the genetic modification); and reduced, or abolished, expression of the peptides (i.e., by complete or partial gene deletion, substitution, insertion, etc.). For example, the action of Pomc peptides can be decreased by blocking or reducing the production of the peptides, "knocking out" the gene or a portion of the gene encoding the peptides, reducing peptide activity, or inhibiting the activity of the peptides.

In one embodiment of the present invention, a non-human animal of the present invention is genetically modified by modification of a nucleic acid sequence within one (i.e., heterozygous) or both (i.e., homozygous) alleles of the Pomc locus, wherein such modification can include, but is not limited to, a deletion, an insertion, a substitution and/or an inversion within the one or more nucleotides in the Pomc locus. In one embodiment, the genetic modification is in a nucleic acid sequence that includes exon 3 of the Pomc locus, such modification resulting in a decrease in Pomc peptide action in the animal. In another embodiment, the genetic modification is in a region of the Pomc locus other than exon 3, whereby the modification results in a decrease in Pomc peptide action in the animal. Such other regions include exon 1, exon 2 or a regulatory region of the Pomc locus. According to the present invention, a regulatory region of a gene includes any regulatory sequences that control the expression of nucleic acid molecules, including promoters, enhancers, transcription termination sequences, sequences that regulate translation, and origins of replication.

In a preferred embodiment of the present invention, a non-human animal of the present invention is genetically modified by deletion of a nucleic acid sequence within one or both alleles of the Pomc locus, wherein the deletion results in a reduction or absence, respectively, of expression of Pomc peptides by the animal. In one embodiment, such a genetic modification is a deletion of a nucleic acid sequence comprising exon 3 of Pomc. In another embodiment, the genetic modification is a deletion of exon 3 of Pomc. In yet another embodiment, the genetic modification is a deletion of a portion of exon 3 of Pomc sufficient to reduce or prevent expression of Pomc peptides by at least one allele and more preferably, by both alleles, of the Pomc locus of the animal.

In one embodiment of the present invention, the genetically modified non-human animal is a mouse, also referred to herein as a POMC homozygous mutant mouse. In this embodiment, the genetic modification is preferably a deletion from the genome of a nucleic acid sequence comprising SEQ ID NO:7, although any genetic modification of the Pomc locus as described above is encompassed by the present invention. SEQ ID NO:7 represents exon 3 of the mouse (i.e., Mus musculus) Pomc locus and can be located in the GenBank database as GenBank Accession No. J00612. SEQ ID NO:7 encodes an amino acid sequence represented herein as SEQ ID NO:8. Preferably, the genetic modification in the mouse is a deletion from the genome of exon 3 of Pomc (SEQ ID NO:7).

The genetically modified non-human animal of the present invention can be characterized by several phenotypes which result from the reduction or absence in Pomc peptide action in the animal. Such phenotypic characteristics include: obesity, a defect in adrenal development, and/or altered pigmentation. In addition, the present inventors have discovered that such a genetically modified non-human animal has measurably increased serum leptin levels as compared to a wild-type sibling of the animal. Other phenotypic characteristics associated with the genetic modification include: an increased food uptake as compared to a wild-type sibling of the animal and/or measurably reduced serum levels of a hormone selected from the group of corticosterone, aldosterone and epinephrine as compared to a wild-type sibling of the animal.

As used herein, a wild-type sibling, or wild-type littermate, is an animal which is born to the same or genetically identical parents as a genetically modified animal described herein, and preferably, is born in the same litter as a genetically modified animal described herein, but which did not inherit a genetically modified allele at the Pomc locus. Such an animal is essentially a normal animal and is useful as an age-matched control for the methods described herein.

According to the present invention, a non-human animal can be genetically modified by any method which results in the desired effect (i.e., reduction in Pomc peptide action in the animal). Such methods are typically molecular techniques, and include, but are not limited to, any deletion of at least a portion of the Pomc locus in the animal, any insertion of a non-Pomc sequence into at least a portion of the Pomc locus in the animal, or any substitution of at least a portion of the Pomc locus in the animal with any non-Pomc sequence or mutated Pomc sequence, sufficient to reduce Pomc peptide action in the animal. For example, a Pomc locus in the genome of an animal (or an embryonic cell) can be genetically modified by inserting into at least one allele of the Pomc locus of the animal or cell an isolated nucleic acid molecule which encodes at least a section of the Pomc gene. At least a portion of this isolated section of the Pomc gene is mutated (i.e., by deletion of the portion, substitution of the portion with another, non-Pomc sequence, or insertion of a non-Pomc sequence into the section of Pomc), such that when the isolated nucleic acid molecule is inserted into the endogenous Pomc locus of the animal or cell, the animal or cell will have a reduction or elimination in the action of Pomc peptides as described above. As another example, in one embodiment of the invention, a genetically modified mouse is produced by inserting into the genome of an embryonic stem (ES) cell an isolated nucleic acid molecule (e.g., a targeting vector) having an isolated nucleic acid sequence encoding the murine Pomc gene. In this isolated nucleic acid sequence, exon 3 of the murine Pomc gene has been deleted and replaced with a non-Pomc nucleic acid sequence (e.g., a marker sequence, such as a neomycin cassette). The isolated nucleic acid molecule is preferably designed such that when the molecule is injected into embryonic stem (ES) cells, the isolated nucleic acid molecule will integrate into the genome of the cells, preferably at the endogenous Pomc locus (i.e., targeted integration).

Techniques for achieving targeted integration of an isolated nucleic acid molecule into a genome are well known in the art and are described, for example in "Manipulating the Mouse Embryo", supra. For example, the isolated nucleic acid molecule can be engineered into a targeting vector which is designed to integrate into a host genome. According to the present invention, a targeting vector is defined as a nucleic acid molecule which has the following three features: (1) genomic sequence from the target locus in the host genome to stimulate homologous recombination at that locus; (2) a desired genetic modification within the genomic sequence from the target locus sufficient to obtain the desired phenotype; and (3) a selectable marker (e.g., an antibiotic resistance cassette, such as G418, neomycin, or hygromycin resistance cassettes). Such targeting vectors are well known in the art. Following introduction of the isolated nucleic acid molecule of the targeting vector into the ES cells, ES cells which homologously integrate the isolated nucleic acid molecule are injected into mouse blastocysts and chimeric mice are produced. These mice are then bred onto the desired mouse background to detect those which transmit the mutated gene through the germ line. Heterozygous offspring of germline transmitting lines can then be mated to produce homozygous progeny.

Mice which carry one or more mutated Pomc alleles can be identified using any suitable method for evaluating DNA. For example, genotypes can be analyzed by PCR and confirmed by Southern blot analysis as described (Sambrook et al., 1988, Molecular Cloning: A Laboratory Manual, Cold Spring Harbor Press, Cold Spring Harbor Laboratory, Cold Spring Harbor, N.Y. or Current Protocols in Molecular Biology (1989) and supplements).

According to the present invention, an isolated nucleic acid molecule suitable for use in the present invention (e.g., suitable for use in a targeting vector according to the invention) is typically produced using recombinant DNA technology (e.g., polymerase chain reaction (PCR) amplification, cloning) or chemical synthesis. DNA comprising the desired nucleic acid sequence (e.g., the Pomc locus, modified or unmodified) may be created, for example, by using polymerase chain reaction (PCR) techniques or other cloning techniques. The template can be a genomic or cDNA library isolated from central nervous system or pituitary tissue. Such methodologies are well known in the art (Sambrook et al., supra).

Isolated nucleic acid molecules useful in the present invention can be modified by nucleotide insertions, deletions, and substitutions (e.g., nucleic acid homologues) in a manner such that the modifications produce the desired effect (e.g., a deletion or substitution of a portion of a Pomc gene sufficient to reduce POMC action in an animal when the nucleic acid molecule is integrated into the animal's genome). An isolated nucleic acid molecule encoding Pomc peptides can include degeneracies. As used herein, nucleotide degeneracies refers to the phenomenon that one amino acid can be encoded by different nucleotide codons. Thus, the nucleic acid sequence of a nucleic acid molecule that encodes a Pomc peptide of the present invention can vary due to degeneracies.

One embodiment of the present invention relates to a method for studying the molecular and biochemical events associated with body weight gain and loss, and particularly, with such events that are associated with obesity. More particularly, such a method includes the steps of: (a) harvesting cells, tissues or body fluids from a genetically modified non-human animal of the present invention; and, (b) comparing the cells, tissues or body fluids from the genetically modified non-human animal to cells, tissues or body fluids from a wild-type sibling of the genetically modified non-human animal. The step of harvesting is performed using any of the well known methods of harvesting cells, tissues and/or body fluids from an animal, and depend on the tissues to be studied and the status of the experiment to be performed. For example, cells can be harvested by biopsy, dissection, or lavage; tissues can be harvested by surgery, biopsy or dissection; and body fluids can be harvested by withdrawal, swiping, or lavage.

The step of comparing is performed by an assay that is suitable for the tissue to be evaluated and the goal of the experiment. For example, suitable assays which might be performed on the cells, tissues, and/or body fluids of a genetically modified non-human animal of the present invention include, but are not limited to: morphological examination of the cells, tissues or body fluids; histological examination of the cells, tissues or body fluids; evaluation of Pomc peptide biological activity in the animal; evaluation of free fatty acid metabolism in the animal; evaluation of lipolysis and fatty acid sequestration in the animal; evaluation of weight gain or loss in the animal; evaluation of hormone levels in the animal; evaluation of blood biochemistry in the animal. A variety of such assays are well known in the art.

Another embodiment of the present invention relates to a method to identify POMC compounds, and particularly, homologues and mimetics, for use in regulating peripheral and central pathways of energy homeostasis. Such a method includes screening a compound to be evaluated for its ability to stimulate lipolysis and/or to inhibit fatty acid uptake by adipocytes, and in particular, to control body weight in a genetically modified non-human animal of the present invention. Such a method can be performed in vitro (e.g., by using cells, tissues or body fluids of the genetically modified animal as described above) or in vivo (e.g., by administering regulatory compounds to a genetically modified animal of the present invention and evaluating the effects of such compounds in vivo. Regulatory compounds identified by this method are useful for controlling body weight in an animal, and may have additional beneficial therapeutic effects on disorders and conditions related to excess body weight in an animal. In particular, the method of the present invention includes the steps of: (a) administering a compound to be evaluated to a genetically modified non-human animal which comprises a genetic modification within two (both) alleles of its Pomc locus, wherein the genetic modification results in an absence of Pomc peptide action in the animal; and, (b) evaluating physiological and pathological changes in the genetically modified non-human animal as compared to a non-human animal selected from the group of: (i) a second genetically modified non-human animal comprising a genetic modification within at least one allele of its pomc1 locus, wherein the genetic modification results in a reduction in proopiomelanocortin (Pomc) peptide action in the animal; and (ii) a third non-human animal having a genome comprising a wild-type pomc1 locus at two (i.e., both) alleles.

As discussed previously herein, the present inventors have discovered that when the POMC homozygous mutant mice described herein were treated peripherally with a stable α-MSH agonist, these mice lost over 40% of their excess weight after two weeks, whereas wildtype non-obese mice did not lose significant weight. The present inventors have shown that the weight changes in Pomc mutant mice are not simply regulated through feeding behavior, but rather through both central and peripheral actions of melanocortins. Based on in vivo experiments described herein, the present inventors have shown MSH to be a peripherally acting, adiposity regulating hormone.

The data from previous investigators which suggested a central nervous system (hypothalamic) effect of melanocortins on appetite, and the present inventors' data which demonstrates a peripheral action of melanocortins on fatty acid metabolism, have led the present inventors to propose the following mechanism for the weight loss observed in the Pomc mutant mice as a result of administration of an MSH agonist. Without being bound by theory, the present inventors' believe that the method of the present invention, while it may have some impact on the central melanocortinergic pathways of energy homeostasis, is primarily effective for regulating adipocyte/fatty acid metabolism. In support of this belief, it is noted that the molar concentration of a melanocortin agonist that would be necessary to effect a transient decrease in food intake (i.e., via the central nervous system) is one hundred-fold higher than that required to accomplish weight reduction in obese mice or to prevent weight gain in a mouse that is genetically predisposed to obesity. Also without being bound by theory, the present inventors believe that under some physiological conditions, an organism is compelled to both suppress appetite and to metabolize fat stores from peripheral adipose tissue. Secretion of melanocortins in the hypothalamus serves both to suppress appetite and, after diffusion to the periphery, to stimulate lipolysis from adipocytes. It is significant that the amount of melanocortin agonist necessary to effect a decrease in appetite when applied directly to the hypothalamus is equivalent to the amount necessary to effect a decrease in fatty acid accumulation when applied peripherally. In the normal course of events, melanocortins are produced in the hypothalamus and then diffuse to the periphery. It follows that cells in the hypothalamus should be less sensitive to melanocortins and cells in the periphery more sensitive. Again, this is consistent with the present inventors' findings that the amount of peripherally administered melanocortin agonist needed to effect body weight homeostasis is two orders of magnitude lower than that required to effect a change in appetite.

The discovery by the present inventors of the present methods and compositions provides particular advantages compared to previously described methods of weight control, in that when the POMC compounds as described herein are applied peripherally according to the method of the present invention, rather than produced centrally, the effects of the compound will be restricted to the periphery, since the central nervous system concentrations will not approach those necessary to have a significant impact on hyperphagia. Thus, the method of the present invention takes advantage of the differential sensitivities of the central nervous system and peripheral tissues to POMC compounds, such as melanocortins. By applying a POMC compound as described herein peripherally, when the naturally occurring form of such compound is normally produced centrally, peripheral effects are stimulated while central nervous system effects are mitigated. For example, a change in the metabolism of fatty acids may be affected without alteration of the appetite of the patient.

According to the present invention, to "control" or "regulate" body weight, can refer to reducing body weight, increasing body weight, reducing the rate of weight gain, or reducing the rate of weight loss. In a preferred embodiment, the mouse model of the present invention is useful for identifying compounds and developing protocols for reducing body weight and/or reducing weight gain in an animal, and more particularly, to treating or ameliorating obesity in patients at risk for or suffering from obesity.

The first step of the method of the present invention includes the step of administering to the genetically modified non-human a regulatory compound to be evaluated. According to the present invention, suitable compounds to be evaluated for regulatory activity in the present method preferably include compounds which have an unknown regulatory activity or an undetermined level of regulator activity, at least with respect to the ability of such compounds to regulate body weight and/or biochemical or molecular events associated with regulation ofbodyweight, as well as compounds which have a known ability to regulate body weight and or biochemical or molecular events associated with regulation of body weight and analogs of such known compounds. Particularly preferred putative regulatory compounds to test in the method of the present invention include any proopiomelanocortin (Pomc) compounds, which preferably include a homologue of a Pomc peptide, a peptide or non-peptide mimetic of a Pomc peptide, a fusion protein including a Pomc peptide, or a recombinant nucleic acid molecule encoding such a Pomc peptide, fragment, homologue, peptide mimetic, or fusion protein thereof. It is noted, however, that other non-POMC compounds can also be evaluated in the method of the present invention. One example of such a non-POMC compound is leptin. In a preferred embodiment, the POMC compound is a melanocyte stimulating hormone (MSH) compound. The method of the present invention is also useful for evaluating the relative benefits of compounds which are believed or known by the present inventors to be capable of regulating body weight in an animal. Such compounds include several POMC compounds, including Pomc peptides, fragments of such peptides, homologues of such peptides, and mimetics of such peptides. In the case of compounds which are believed or known to be regulators of body weight, the animal model of the present invention is useful for comparing these compounds to each other or to putative regulatory compounds, and for addressing issues related to dosage, toxicity, and other factors associated with the administration of a compound to an animal.

According to the present invention, the phrase "POMC compound" encompasses any of the following compounds: a Pomc peptide (i.e., a peptide encoded by the Pomc gene), a fragment of such a peptide (including both biologically active and inactive fragments), a homologue of such a peptide, a mimetic (peptide or non-peptide) of such a peptide, a fusion protein comprising such a peptide, and any pharmaceutical salts of such a peptide. In addition, peptides useful as regulatory compounds in the present invention may exist, particularly when formulated, as dimers, trimers, tetramers, and other multimers. Such multimers are included within the scope of the present invention. As used herein, the term "analog", as used in connection with a Pomc peptide according to the present invention, refers generically to any homologue or mimetic (peptide or non-peptide) of a Pomc peptide. Analogs can include both agonists and antagonists of the prototype Pomc peptide. Terms used herein in connection with Pomc genes and proteins (e.g., "compound", "analog", "homologue", "mimetic") can be similarly used with specific Pomc genes and proteins (e.g., an MSH peptide, an MSH compound, an MSH analog, etc.). Homologues and mimetics are described in detail below. In one embodiment of the present invention, a POMC compound is an isolated nucleic acid molecule that encodes a Pomc peptide, a peptide analog thereof, or a fusion protein comprising such a peptide.

Preferably, regulatory POMC compounds that are identified according to the method of the present invention are any compound having one or more of the following properties or identifying characteristics: (1) an ability to bind to a Pomc peptide receptor, and particularly, to a POMC receptor that is expressed in peripheral (as opposed to central nervous system) tissues; and, (2) an ability to stimulate lipolysis and/or to inhibit the uptake of fatty acids by adipocytes. Particularly preferred POMC compounds for use in the present method include homologues and mimetics of naturally occurring Pomc peptides which have substantially similar, or even more preferably, enhanced, properties or identifying characteristics as compared to the naturally occurring (i.e., prototype) Pomc peptide (e.g., agonists). Such properties or identifying characteristics include: (1) enhanced ability to bind to a Pomc peptide receptor, and particularly, to a POMC receptor that is expressed in peripheral (as opposed to central nervous system) tissues; (2) enhanced serum half-life (i.e., enhanced stability under physiological conditions); and/or (3) enhanced ability to stimulate lipolysis and/or to inhibit the uptake of fatty acids by adipocytes. In one embodiment of the present invention, if it is desirable to block the action of a naturally occurring POMC-peptide (i.e., an antagonist), such as in a method to regulate a patient's ability to gain weight or avoid undesirable weight loss, the desirable properties of a POMC homologue or mimetic include a decreased ability to stimulate lipolysis and/or to inhibit the uptake of fatty acids by adipocytes, while serum half-life and receptor binding abilities (for blocking, but not activating the receptor) are preferably substantially similar or enhanced compared to the naturally occurring peptide.

In a preferred embodiment, the POMC compound can include any peptide that has an amino acid sequence which includes the amino acid sequence represented herein by SEQ ID NO:1 (EHFRW), or a homologue or mimetic thereof. In another embodiment, a preferred POMC compound includes, but is not limited to, a melanocortin and/or a lipocortin, fragments of such peptides, homologues of such peptides, mimetics (peptide or non-peptide) of such peptides, fusion proteins comprising such peptides, and any pharmaceutical salts of such peptides. Melanocortins include, but are not limited to: adrenocorticotrophin (ACTH), α-melanocyte stimulating hormone (α-MSH), β-melanocyte stimulating hormone (β-MSH) and γ-melanocyte stimulating hormone (γ-MSH); and β-endorphin. Preferred melanocortins include melanocyte stimulating hormones (MSH), fragments of such peptides, homologues of such peptides, mimetics (peptide or non-peptide) of such peptides, fusion proteins comprising such peptides, and any pharmaceutical salts of such peptides. Particularly preferred MSH peptides include α-MSH, β-MSH and γ-MSH, fragments of such peptides, homologues of such peptides, mimetics (peptide or non-peptide) of such peptides, fusion proteins comprising such peptides, and any pharmaceutical salts of such peptides.

The amino acid sequence of human α-MSH is:

Ac-Ser-Tyr-Ser-Met-Glu-His-Phe-Arg-Trp-Gly-Lys-Pro-Val-NH$_2$; and is represented herein by SEQ ID NO:2. It should be noted that since amino acid sequencing and nucleic acid sequencing technologies are not entirely error-free, any sequences presented or referenced herein, at best, represent apparent sequences of Pomc peptides, homologues, peptide mimetics, and nucleic acid sequences encoding such peptides, useful in the present invention.

As discussed above, particularly preferred POMC compounds which may be evaluated and identified using the method of the present invention are homologues or mimetics of Pomc peptides, also referred to herein collectively as analogs of Pomc peptides, which have enhanced properties as compared to the naturally occurring Pomc peptide, such properties including: (1) enhanced ability to bind to a Pomc peptide receptor, and particularly, to a POMC receptor that is expressed in peripheral (as opposed to central nervous system) tissues; (2) enhanced serum half-life (i.e., enhanced stability under physiological conditions); and/or (3) enhanced ability to stimulate lipolysis and/or to inhibit the uptake of fatty acids by adipocytes.

As used herein, the term "homologue" is used to refer to a peptide which differs from a naturally occurring peptide (i.e., the "prototype") by minor modifications to the naturally occurring peptide, but which maintains the basic peptide and side chain structure of the naturally occurring form. Such changes include, but are not limited to: changes in one or a few amino acid side chains; changes one or a few amino acids, including deletions (e.g., a truncated version of the peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. Preferably, a homologue has either enhanced or substantially similar properties compared to the naturally occurring Pomc peptide as discussed above (i.e., agonists), although peptides with diminished properties (i.e., antagonists) are also encompassed by certain embodiments of the present invention.

POMC homologues can be the result of natural allelic variation or natural mutation. A naturally occurring allelic variant of a nucleic acid encoding Pomc peptide (or a protein comprising an Pomc peptide) is a gene that occurs at essentially the same locus (or loci) in the genome as the gene which encodes such Pomc peptide, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

As used herein, the term "mimetic" is used to refer to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

Such mimetics can be designed, selected and/or otherwise identified using a variety of methods known in the art. Various methods of drug design, useful to design mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety. A POMC mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Preferred POMC analogs (homologues or mimetics) for evaluation in the method of the present invention include POMC analogs of the melanocortins. Particularly preferred POMC analogs for evaluation in the method of the present invention include analogs of MSH proteins (peptides).

Numerous analogs (homologues and mimetics) of Pomc peptides, and particularly, of melanocortins, have been previously described in the art, and all are intended to be encompassed for use in the method of the present invention. For example, such analogs are disclosed in Hadley et al., 1986, "α-Melanotropin analogs for Biomedical Applications", *Neural and Endocrine Peptides and Receptors*, T. W. Moody, ed., Plenum Publ. Corp., NY, pp. 45–56; U.S. Pat. No. 4,649,191 to Hruby, U.S. Pat. No. 4,918,055 to Hruby et al., U.S. Pat. No. 5,674,839 to Hruby et al., U.S. Pat. No. 5,683,981 to Hadley et al., U.S. Pat. No. 5,714,576 to Hruby et al., and U.S. Pat. No. 5,731,408 to Hruby et al., each of which is incorporated herein by reference in its entirety, particularly with regard to the structures of analogs of melanocortins and especially, MSH analogs, disclosed therein, as well as to the methods of producing such analogs. An MSH analog suitable for use in the method of the present invention is exemplified in Examples 2–5 (i.e., [Ac-Cys$^4$, D-Phe$^7$, Cys$^{10}$] α-MSH), although it will be apparent to those of skill in the art that the present invention is not limited to this particular MSH analog.

Preferred MSH analogs include, but are not limited to, the following analogs:

(a) cyclic and linear α-MSH fragment analogs of the core sequence of αMSH, Met$^4$-Glu$^5$-His$^6$-Phe$^7$-Arg$^8$-Trp$^9$-Gly$^{10}$ (positions 4–10 of SEQ ID NO:2), having modifications including but not limited to: (1) replacement of Met$^4$ with Nle; (2) replacement of L-Phe$^7$ with D-Phe$^7$; (3) cyclization between positions 4 and 10; and/or (4) presence of Lys$^{11}$ in analog at position 10 (See U.S. Pat. Nos. 5,674,839 and 5,714,576 to Hruby et al., supra);

(b) linear and cyclic analogs of αMSH having the general formula:

Ac-[Nle$^4$, X$_{aa}$$^5$, His$^6$, X$_{aa}$$^7$, Arg$^7$, Trp$^9$, X$_{aa}$$^{10}$]-NH$_2$      (SEQ ID NO:3)

wherein X$_{aa}$$^5$ is either Glu or Asp, X$_{aa}$$^7$ is Phe or D-Phe and X$_{aa}$$^{10}$ is a dibasic amino acid, lysine, ornithine, 2,4,-diaminopropionic acid, or 2,3 diaminopropionic acid (Dpr); and, wherein cyclization is between positions 4 and 10 (See U.S. Pat. Nos. 5,674,839 and 5,714,576 to Hruby et al., supra);

(c) cyclic analogs of α-MSH using pseudoisosteric replacement of Met$^4$ and Gly$^{10}$ with Cys amino acids Ac-[Cys$^4$, Cys$^{10}$]α-MSH$_{1-13}$NH$_2$ (See U.S. Pat. Nos. 5,674,839 and 5,714,576 to Hruby et al., supra);

(d) linear analogs of the formula: R$_1$-W-X-Y-Z-R$_2$ (See U.S. Pat. No. 4,918,055 to Hruby et al., supra); wherein
R$_1$ is selected from the group consisting of Ac-Gly—, Ac-Met-Glu—, Ac-Nle-Glu— and Ac-Tyr-Glu—;
W is selected from the group consisting of —His— and —D-His—;
X is selected from the group consisting of —Phe—, —D-Phe—, —Tyr, —D-Tyr—, (-pNO$_2$)D-Phe$^7$—;
Y is selected from the group consisting of —Arg— and —D-Arg—;
Z is selected from the group consisting of —Trp— and —D-Trp—; and,
R$_2$ is selected from the group consisting of —NH$_2$, —Gly-NH$_2$, and —Gly-Lys-NH$_2$;

(e) linear α-MSH analogs having the formula:

Ac-Ser-Tyr-Ser-Xaa-Glu-His-D-Phe-Arg-Trp-Gly-Lys-Pro-Val-NH$_2$      (SEQ ID NO:4), wherein Xaa is selected from the group consisting of Met, Nle, and Cys (See U.S. Pat. No. 4,918,055 to Hruby et al., supra);

(f) linear α-MSH analogs selected from the group consisting of:
[Nle$^4$, D-Phe$^7$]-α-MSH;
[Nle$^4$, D-Phe$^7$]-α-MSH$_{4-10}$;
[Nle$^4$, D-Phe$^7$]-α-MSH$_{4-11}$;
[Nle$^4$, D-Phe$^7$,D-Trp$^9$]-α-MSH$_{4-11}$; and,
[Nle$^4$, D-Phe$^7$]-α-MSH$_{4-9}$ (See U.S. Pat. No. 4,918,055 to Hruby et al., supra); and, (g) cyclic bridged analogs of α-MSH having the general structure (See U.S. Pat. No. 5,683,981 to Hadley et al., supra)

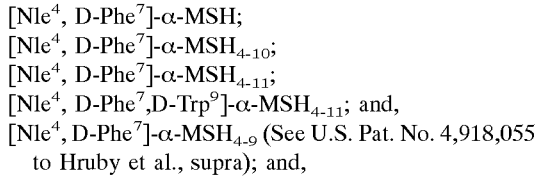

wherein AA$^5$ may be either a L- or D- amino acid having an omega amino or carboxyl group in the side chain, e.g., α,γ-diaminopropionic acid, α,γ-diaminobutyric acid, Orn, Lys, α,β-aminoadipic acid, α-aminopimelic acid, or higher homologs, Glu or Asp;

wherein AA$^{10}$ may be diaminopropionic acid, α,γ-diaminobutyric acid, Orn, Lys, α,β-aminoadipic acid, α-aminopimelic acid, or higher homologs, Glu or Asp;

wherein R$_1$ is the designation α-MSH$_{1-3}$NH$_2$, α-MSH$_{1-12}$NH$_2$, α-MSH$_{1-11}$NH$_2$, α-MSH$_{4-13}$NH$_2$, or α-MSH$_{4-10}$NH$_2$;

wherein AA$^{11}$ may be L- or D- amino acid having an omega-amino or carboxyl group in the side chain, e.g., α,β-diaminopropionic acid; α,γ-diaminobutyric acid, Orn, Lys, α-aminoadipic acid, α-aminopimelic acid, or higher homologs, Glu or Asp;

wherein R$_2$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$; and, wherein Xxx may be from 1 to 5 a-amino acid residues each of which may be of L- or D- configuration, or a linear or branched chain spacer.

MSH analogs which may be particularly useful as αMSH antagonists (See U.S., Pat. No. 4,649,191 to Hruby et al., supra) include, but are not limited to:

(a) cyclic analogs having the general formula (See U.S. Pat. No. 5,731,408 to Hadley et al., supra):

(SEQ ID NO: 5)

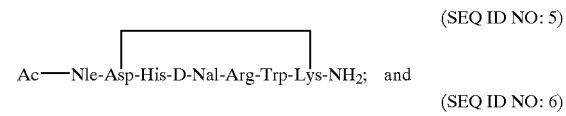

(SEQ ID NO: 6)

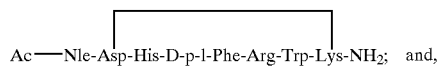

(b) cyclic analogs having the general formula (See U.S. Pat. No. 4,649,191 to Hruby et al., supra):

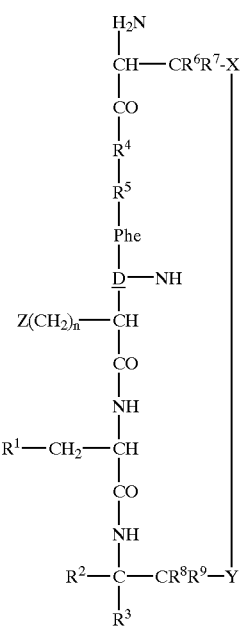
(1)

wherein $R^1$ is a substituted or unsubstituted aromatic radical;
$R^2$ is hydrogen or a methyl group;
$R^3$ is a carboxylate, carboxamide, hydroxymethyl, or aldehyde group;
$R^4$ is glutamic acid, alanine, -amino butyric acid, valine, leucine or isoleucine;
$R^5$ is histidine, glutamic acid, alanine, valine, leucine or isoleucine;
$R^6$ and $R^7$, which may be the same or different, are hydrogen, methyl or lower alkyl having one to five carbon atoms;
$R^8$ and $R^9$, which may be the same or different, are hydrogen, methyl or lower alkyl having one to five carbon atoms;
X and Y are sulfur, methylene, SO or $SO_2$;
Z is $-NH_2$,

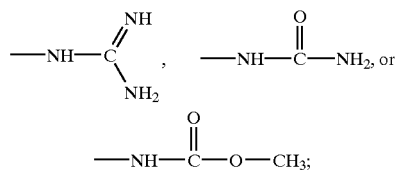

and,
n is an integer greater than or equal to 2;

wherein $R^1$ is phenyl, indole, p-hydroxyphenyl, p-aminophenyl, imidazole, 1-naphthyl adamantyl or alkylphenyl, 2-naphthyl;
$R^2$ is hydrogen or a methyl group;
$R^3$ is a carboxylate, carboxamide, hydroxymethyl, or aldehyde group;
X and Y are sulfur, methylene, SO or $SO_2$;
Z is $-NH_2$,

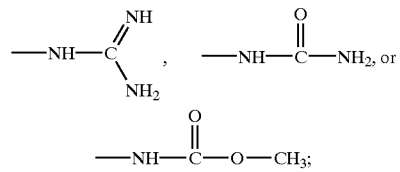

and,
n is an integer greater than or equal to 2; and wherein the cyclized portion of the compound is conformationally restricted in a manner which is compatible with the reactivity of the compound with receptors of the central nervous system.

In one embodiment of the present invention, POMC homologues and mimetics are evaluated for increased or decreased stability and/or increased or decreased biological activity compared to an unmodified Pomc peptide (i.e., a naturally occurring or prototype Pomc peptide). As used herein, the biological activity or biological action of a protein (e.g., a peptide) refers to any function(s) exhibited or performed by a naturally occurring form of the protein as measured or observed in vivo (i.e., in the natural physiological environment of the protein in the organism) or in vitro (i.e., under laboratory conditions, in tissue culture or cell free systems, for example). For example, a biological activity of a protein can include, but is not limited to, hormone activity, protein binding activity, receptor binding activity, calcium binding activity, protein translocation, or DNA binding activity. Modifications of a protein, such as in a homologue or mimetic, which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

In accordance with the present invention, increased stability refers to the property of a POMC homologue or mimetic to have a longer half-life (i.e., have greater stability under physiological conditions, such as in serum), by being more resistant, for example, to proteolytic degradation compared to proteins comprising unmodified Pomc peptides, to higher or lower temperature, to more acidic or basic pH, to higher or lower salt concentrations, to oxidation and/or

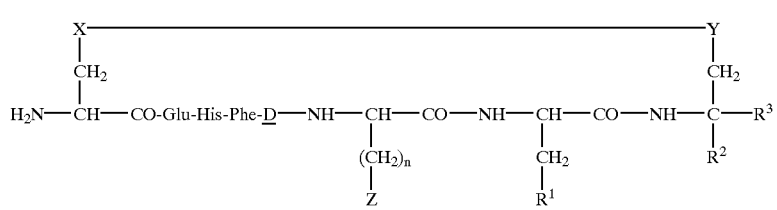
(2)

reduction, to deamidation, and to other forms of chemical degradation. Similarly, decreased stability refers to the property of a mimetic to be less resistant, for example, to such conditions.

According to the present invention, an isolated or biologically pure protein, including peptides and analogs thereof, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. Such methods are described in detail below. It is to be noted that the term "a" or "an" entity refers to one or more of that entity; for example, a compound refers to one or more compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

The compounds useful for evaluation in the method of the present invention may be produced by any method suitable for the production of peptides and/or non-peptide mimetics, and particularly, for Pomc peptides or non-peptide mimetics. For example, such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol.* 289:3–13; Wade et al., 1993, *Australas Biotechnol.* 3(6):332–336; Wong et al., 1991, *Experientia* 47(11–12):1123–1129; Carey et al., 1991, *Ciba Found Symp.* 158:187–203; Plaue et al., 1990, *Biologicals* 18(3): 147–157; Bodanszky, 1985, *Int. J. Pept. Protein Res.* 25(5):449–474; or H. Dugas and C. Penney, BIOORGANIC CHEMISTRY, (1981) at pages 54–92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture. Methods for synthesizing MSH analogs, for example, are described in detail in U.S. Pat. No. 4,649,191 to Hruby, supra, U.S. Pat. No. 4,918,055 to Hruby et al., supra, U.S. Pat. No. 5,674,839 to Hruby et al., supra, U.S. Pat. No. 5,683,981 to Hadley et al., supra, U.S. Pat. No. 5,714,576 to Hruby et al., supra, and U.S. Pat. No. 5,731,408 to Hruby et al., supra, all of which are incorporated herein by reference in their entirety.

If larger quantities of a Pomc peptide are desired, the peptide (or peptide analog thereof) can be produced using recombinant DNA technology, although for proteins of this small size (i.e., peptides), peptide synthesis is generally more preferred. A peptide can be produced recombinantly by culturing a cell capable of expressing the peptide (i.e., by expressing a recombinant nucleic acid molecule encoding the peptide) under conditions effective to produce the peptide, and recovering the peptide. Such techniques are well known in the art and are described, for example, in Sambrook et al. supra.

In the practice of the method of the present invention, it is useful, although not essential, to prepare formulations comprising an amount of at least one regulatory compound to be evaluated according to the present invention, either alone or in combination with a pharmaceutically acceptable salt and/or complexed with another suitable carrier (described below). Such formulations can be formulated for any route of administration, including, but not limited to, parenteral administration and transdermal administration. For example, formulations to be evaluated can be formulated in an excipient that the animal to be treated can tolerate. Examples of such excipients include water, saline, phosphate buffered solutions, Ringer's solution, dextrose solution, Hank's solution, polyethylene glycol-containing physiologically balanced salt solutions, and other aqueous physiologically balanced salt solutions. Nonaqueous vehicles, such as fixed oils, sesame oil, ethyl oleate, or triglycerides may also be used.

The formulations comprising one or more desired compounds typically contain from about 0.1% to 90% by weight of the active compound, preferably in a soluble form, and more generally from about 0.1% to 1.0%.

In one embodiment of the present invention, a pharmaceutically acceptable carrier can include additional compounds that increase the half-life of a formulation in the treated animal. Suitable carriers include, but are not limited to, polymeric controlled release vehicles, biodegradable implants, liposomes, bacteria, viruses, other cells, oils, esters, and glycols.

In one embodiment of the present invention, a formulation can include a controlled release composition that is capable of slowly releasing the formulation into an animal. As used herein, a controlled release composition comprises a regulatory compound to be evaluated as described herein in a controlled release vehicle. Suitable controlled release vehicles include, but are not limited to, biocompatible polymers, polymeric matrices, capsules, microcapsules, microparticles, bolus preparations, osmotic pumps, diffusion devices, liposomes, liposheres, and transdermal delivery systems. Other controlled release compositions of the present invention include liquids that, upon administration to an animal, form a solid or a gel in situ. Preferred controlled release compositions are biodegradable (i.e., bioerodible).

According to the present invention, an effective administration protocol (i.e., administering a regulatory compound or a formulation comprising such a compound in an effective manner) comprises suitable dose parameters and modes of administration that are not toxic to the animal, and which would reasonably be expected to provide a measurable change in the body weight in the animal when administered one or more times over a suitable time period, if the compound is capable of regulating body weight. Such a dose and administration protocol can easily be evaluated based on the data provided by the present inventors regarding the use an MSH analog to control body weight, for example, although it is well within the ability of one of skill in the art to establish a suitable dose and administration protocol for evaluating the ability of a compound to regulate body weight in a genetically modified non-human animal of the present invention. Effective dose parameters can be determined using methods standard in the art for a particular animal and condition. Such methods include, for example, determination of survival rates, side effects (i.e., toxicity) and other health factors associated with, or in addition to the amount of body weight loss or gain desired in the animal. In particular, the effectiveness of dose parameters of a formulation of the present invention when used to control body weight can be determined by assessing response rates. Such response rates refer to the percentage of treated animals in a population of animals that respond with either partial or complete loss of excess weight, or a reduction in the rate of weight gain, or alternatively, to a partial or complete gain of lost weight or a reduction in the rate of weight loss, to a level which is considered by those of skill in the art to be sufficient to evaluate the compound for efficacy. Response can be determined by, for example, measuring weight loss over time and/or measuring changes in levels of hormones and other biological indicators of obesity and metabolic control in the animal, for example, leptin.

Modes of administration of a compound or formulation of the present invention include any method of administration which results in delivery of the composition to the peripheral circulation of the animal. Such modes of administration can include, but are not limited to, oral, nasal, topical, transdermal, rectal, and parenteral routes. Parenteral routes can include, but are not limited to subcutaneous, intradermal, intravenous, intraperitoneal and intramuscular routes. In one embodiment, the route of administration is by topical or transdermal administration, such as by a lotion, cream, a patch, an injection, an implanted device (e.g., similar to Norplant), or other controlled release carrier.

In the embodiment where the compound or formulation is to be delivered to a patient in the form of a nucleic acid molecule encoding a peptide compound to be evaluated, the nucleic acid molecules can be delivered to a patient by a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, Science 247, 1465–1468); (b) administering a nucleic acid molecule packaged as a recombinant virus, in a liposome delivery vehicle, or in a recombinant cell (i.e., the nucleic acid molecule is delivered by a viral or cellular vehicle); or (c) administering a recombinant nucleic acid molecule encapsulated within a liposome delivery vehicle.

The second step in the method of the present invention includes evaluating physiological and pathological changes in the homozygous genetically modified non-human animal as compared to a heterozygous genetically modified non-human animal and/or a wild type animal. Such physiological and pathological changes include, but are not limited to, changes in body weight (i.e., increase or decrease), changes in body mass, changes in hair or skin pigmentation, changes in adrenal morphology and/or function, changes in circulating hormone levels (e.g., corticosterone, aldosterone, epinephrine), changes in serum leptin levels, changes in appetite, and any other measurable change in the physiology of the animal. Such changes can be evaluated by well known methods in the art, most of which are exemplified in the Examples section.

Yet another embodiment of the present invention relates to a method of producing a genetically modified non-human animal useful for studying peripheral and central pathways of energy homeostasis. Such a method includes the steps of: (a) introducing into an embryonic stem cell of a non-human animal a targeting vector comprising a Pomc locus containing a deletion of a nucleic acid sequence sufficient to result in a reduction in proopiomelanocortin (Pomc) peptide action in the animal; and, (b) obtaining progeny having the deletion stably incorporated into their genome, wherein the deletion results in a reduction in expression of proopiomelanocortin (Pomc) peptides by the animal. In one embodiment, this method additionally includes the step of obtaining progeny having the deletion stably incorporated into their genome, wherein the deletion results in an absence of expression of Pomc peptides by the animal. This third step can be achieved, for example by mating the progeny of step (b) (i.e., heterozygous animals) with each other to obtain the desired phenotype (i.e., homozygous animals). This method has been described in detail above and are exemplified in the Examples section.

Another embodiment of the present invention is a genetically modified mouse useful for studying peripheral and central pathways of energy homeostasis. The mouse is produced by a method comprising the steps of: (a) isolating from a source of murine genomic DNA a nucleic acid molecule comprising SEQ ID NO:7; (b) deleting a nucleic acid sequence comprising SEQ ID NO:7 from the nucleic acid molecule to form a genetically modified nucleic acid molecule; (c) inserting a selectable marker into the genetically modified nucleic acid molecule to create a targeting vector; (d) transfecting the targeting vector into embryonic stem cells; (e) selecting embryonic stem cells from step (d) which have incorporated the targeting vector by homologous recombination; (f) inserting the embryonic stem cells comprising the targeting vector into non-human animal blastocysts; and, (g) impregnating a female surrogate with the non-human animal blastocysts to produce the genetically modified mouse. Methods for practicing this method have been described in detail previously herein and are exemplified in the Examples section.

Various aspects of the present invention are illustrated in the following examples, which are provided for the purposes of illustration and are not intended to limit the scope of the present invention.

EXAMPLES

Example 1

The following example describes the production of the POMC null mutant mouse of the present invention and demonstrates that Pomc peptides are associated with the regulation of body weight through both central and peripheral mechanisms.

To create a mutant mouse strain lacking all proopiomelanocortin (Pomc) derived peptides, the present inventors designed a targeting vector in which the entire third exon (Notake et al., 1983, *FEBS Lett* 156:67–71; incorporated herein by reference in its entirety) is replaced by a neomycin resistance cassette. Briefly, EcoRI-digested 129/SvEv genomic DNA was cloned into lambda FixII (Stratagene). The resulting library was screened with a 0.3 kb PCR fragment from exon 3 of the mouse Pomcl sequence, and a clone carrying a 9.5 kb fragment containing the mouse Pomcl locus was isolated. For the targeting vector the KnpI-PstI fragment containing the third exon was deleted. This removes all but the first 44 codons for amino acids after the translation start of the pre-pro-protein, or all but the first 18 codons for amino acids of the POMC protein. Targeting vector (20 µg) was used to electroporate $10^7$ RW4 ES cells (Genome Systems). ES cells which homologously integrated the mutated allele were injected into C57BL/6 blastocysts as described (Hogan et al., "Manipulating the Mouse Embryo", Cold Spring Harbor Laboratory Press, 1994). Chimeric mice were mated to 129/SvEvTac females. Heterozygous offspring were mated to generate homozygous mutant mice. Genotypes were analyzed by PCR and confirmed by Southern blot analysis as described (Sambrook et al. ibid.).

FIG. 1A shows schematic diagrams and restriction maps of the mouse Pomc locus, the targeting vector, and the predicted structure of the Pomc locus after homologous recombination. The 0.4kb probe fragment hybridizes to a 9.5 kb EcoRI fragment in the wildtype allele, and to a 3.2kb fragment in the mutant allele (see also FIG. 1B). Restriction sites indicated are EcoRI (E), KpnI (K), and PstI (P). FIG. 1B shows Southern blot analyses of tail DNAs from $F_2$ littermates. The probe used was the 0.4 kb PstI-EcoRI fragment (see FIG. 1A). FIG. 1C shows an RIA analysis of serum ACTH levels in $F_2$ male littermates (measurements in triplicates, one mouse per genotype) (discussed in detail below).

The deleted POMC allele construct was introduced into embryonic stem (ES) cells by electroporation and from there into the mouse germline, generating strain Pomc$^{tm2ute}$. When the mutation was backcrossed into the inbred 129/SvEv background, homozygous Pomc mutants were born to heterozygous parents at one quarter (39 wildtype, 80 heterozygotes, 10 mutants) of the frequency expected for a recessive mutation, indicating that concurrent lack of all of the embryonic derived Pomc peptides is compatible with survival throughout prenatal development in only a fraction of the animals.

Female POMC null mice are fertile and carry heterozygous and wild-type pups to term; male POMC null mice are infertile. When heterozygous POMC males are mated to homozygous Pomc mutant females, homozygous mutant, but not heterozygous, offspring die within the first few hours after birth.

Figure 2A:
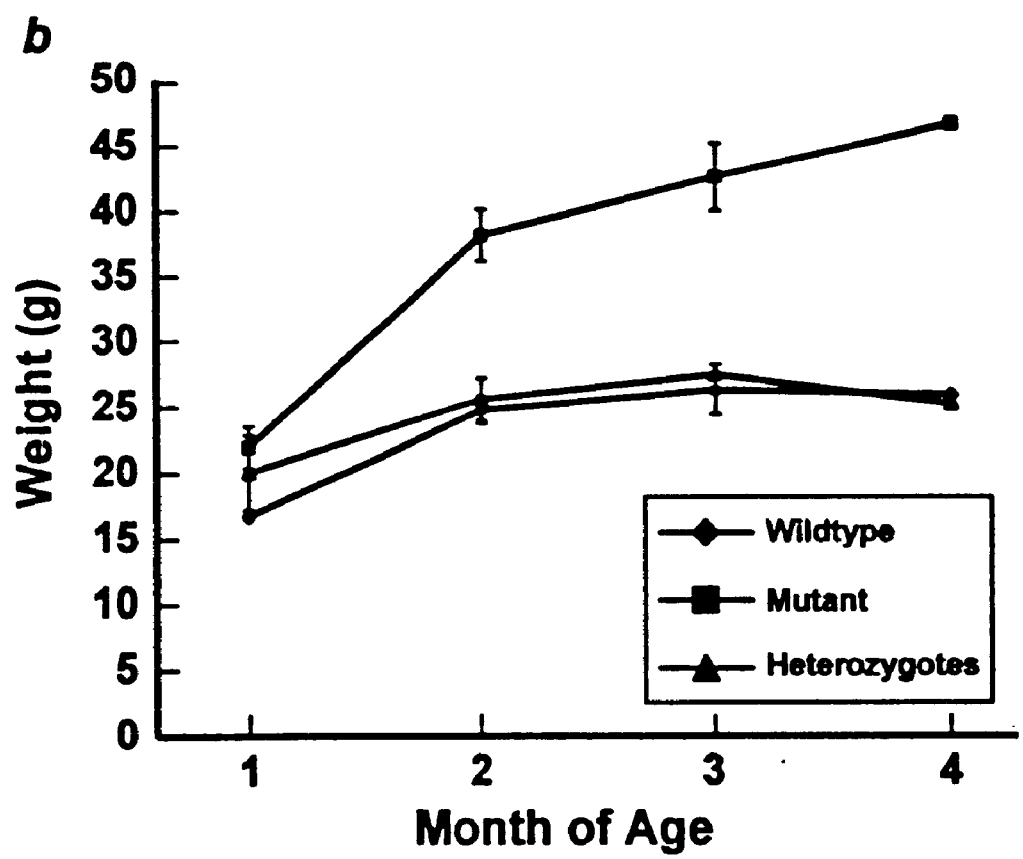
FIG. 2A is a line graph of weight measurements taken from male mice of wildtype and mutant POMC genotype.
Figure 2B:
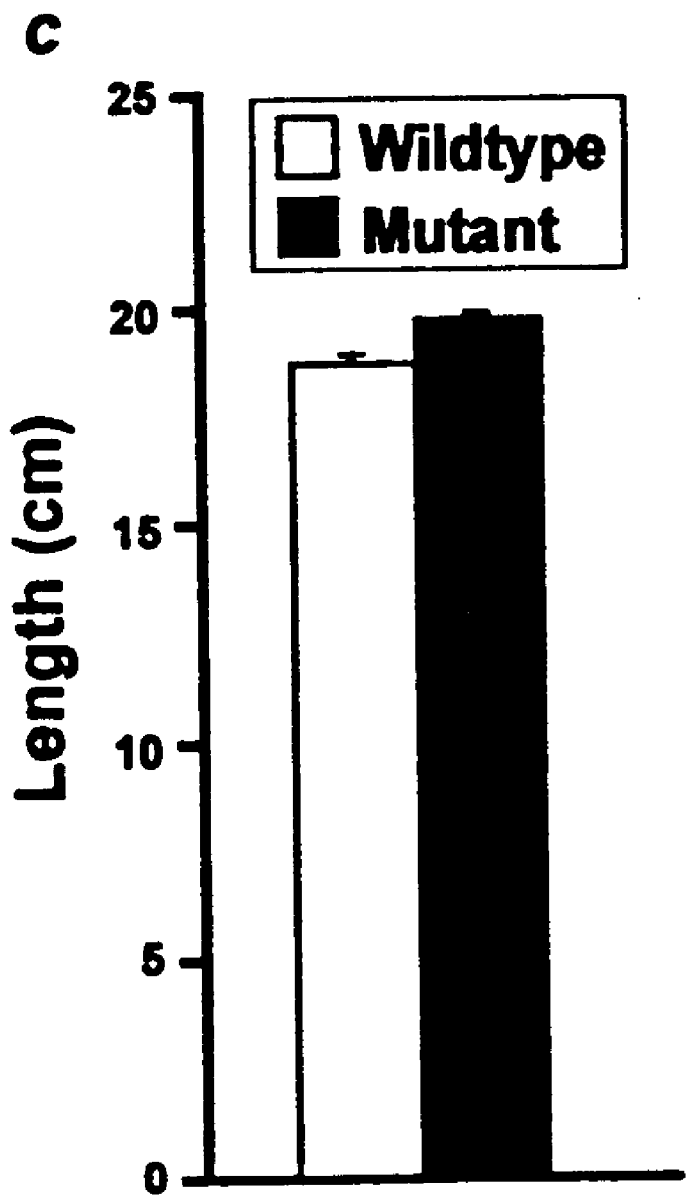
FIG. 2B is a bar graph illustrating that mutant POMC mice show increased linear growth.
Figure 2C:
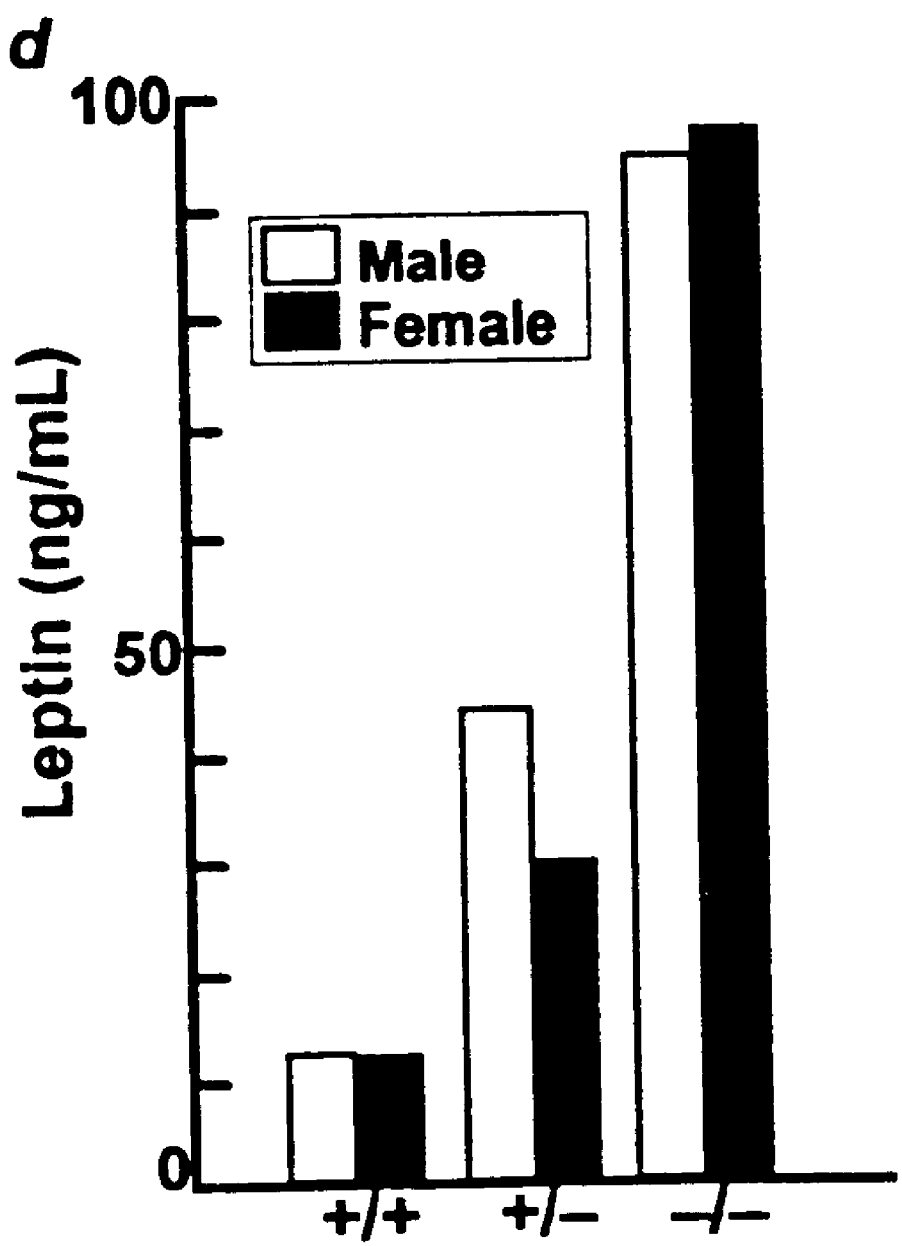
FIG. 2C is a bar graph illustrating that POMC null mice have elevated leptin serum levels.

During the first postnatal month homozygous mutants are superficially indistinguishable from their wildtype littermates. In the second month, mice lacking Pomc peptides start to gain weight visibly, and by the third postnatal month their weights are about twice those of their wildtype littermates (FIG. 2A; weight measurements were taken from male mice of each genotype; at 2 months n=4, P<0.0005; at 3 months n=3, P<0.005). The weight gain is accompanied by both a slight, but significant, increase in body length (FIG. 2B; measurements (snout to root of tail) were taken from 3–4 months old female mice, 6 mice per genotype (P<0.001)) and a large increase in serum leptin levels (FIG. 2C). In this latter experiment, serum leptin levels were determined (in duplicates) from blood samples collected retroorbitally from 6–8 months old, individual, male and female mice. Average weights were 30.9 g for wildtype mice, 31.7 g for heterozygotes, and 55.9 g for homozygotes. Interestingly, heterozygote mice show elevated levels of serum leptin, but do not display increased body weight. The elevated leptin levels in the normal weight heterozygotes suggest a homeostatic balance between leptin levels and Pomc peptide levels: the decreased Pomc peptide levels are compensated by increased leptin. The mechanism and significance of such a relationship suggest a paracrine feedback loop.

Figure 2D:
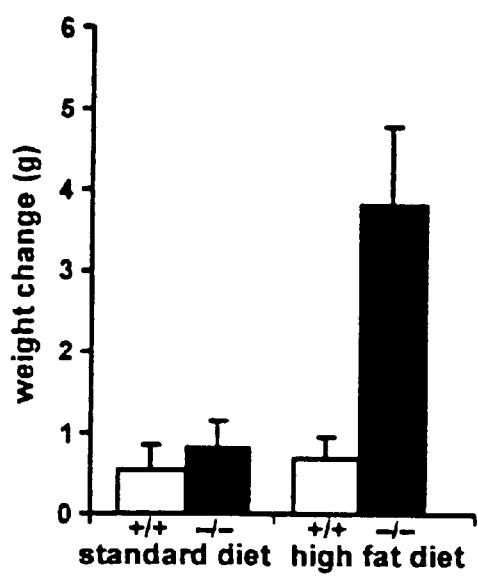
FIG. 2D is a bar graph illustrating weight change for POMC null mice and wildtype mice being fed a standard diet or a high fat diet.
Figure 2E:
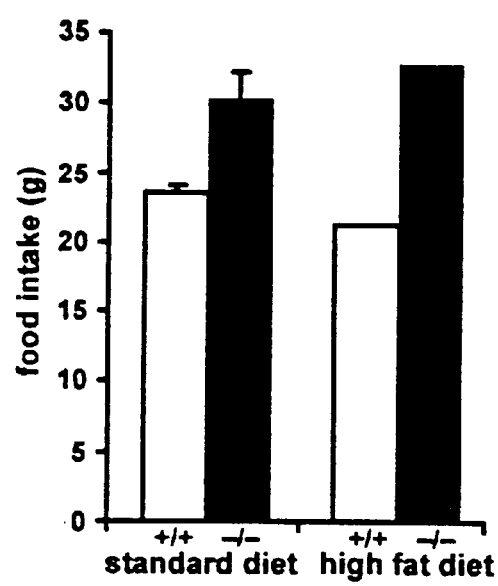
FIG. 2E is a bar graph illustrating food intake for POMC null mice and wildtype mice being fed a standard diet or a high fat diet.

It was also noticed that the Pomc mutant mice raised on a high fat breeder chow gained weight faster than mice raised on standard chow. Wildtype and mutant females (3 per test group) were given unlimited access either to standard or to breeder chow (4.5% and 9% fat, respectively). FIGS. 2D and 2E show weight change (2D) and food intake (2E) during one week. Food intake in the "high fat diet" groups was measured in bulk for all three mice. FIG. 2D shows that the mutant mice gained 3 grams more per week on a high fat diet versus a standard diet (3.8 g versus 0.8 g), while wildtype mice gained 0.2 g more on a high fat diet versus a standard diet (0.7 g versus 0.5 g). FIG. 2E shows that the food intake by Pomc mutants increased with high fat diet by 2.4 g (30.3 g versus 32.7 g), while the food intake by wildtype littermates decreased with high fat diet by 2.2 g (23.5 g versus 21.3 g). Under either dietary condition mutant mice lacking POMC have an increased food intake compared to wildtype littermates. These results suggest that POMC derived peptides mediate both food intake and bodily food deposit. Wildtype mice regulate their food intake according to the diet, i.e., they decrease intake with a higher caloric supply, and they adjust their metabolism (food deposit versus burning) to keep their body weight constant. In contrast, mice lacking POMC show a deficit in both of these aspects with the result of increased body weight: they have an increased food uptake and they lack the ability to catabolize dietary fat.

Another visible difference between POMC null mutant mice and the wildtype mice is the yellowish pigmentation of mutant mice (data not shown), which is especially pronounced on the belly. MC1-R in melanocytes is normally stimulated by α-MSH, resulting in synthesis of eumelanin (black/brown) pigment (Burchill et al., 1986, *J. Endocrinol.* 109:15–21). Antagonism of MC1-R by the agouti-signaling protein (ASP) overexpressed in $A^y$ mice results in whole body yellow coat color (Lu et al., 1994, *Nature* 371:799–802). A loss-of-function mutation in the Mc1r gene in the recessive yellow mouse (e/e) (Robbins et al., 1993, *Cell* 72:827–834) and in cattle (Joerg et al., 1996, *Mamm. Genome* 7:317–318) causes yellow coat and red coat, respectively. The human patients with POMC null mutations have red hair as well (Krude et al., ibid.). In the POMC null mice, the change in pigmentation is subtle, in that the coat covering the sides and belly is more yellow than in wildtype littermates, and the tips of the hairs at the back have a yellowish tinge. These pigmentation differences in mutants become more pronounced during adulthood. The fact that in the mouse, lack of the ligand (Pomc) does not result in a phenotype congruent with lack or antagonism of MC1-R, suggests the presence of other ligands for this melanocortin receptor. Alternatively, this result could be explained if there is a ligand-independent constitutive activity of the receptor.

Next, the effect of a complete lack of ACTH on adrenal function was determined. Serum corticosterone levels (FIG. 3A) were determined by RIA from blood samples collected retroorbitally from 6–7 month old mice (n=7 for wildtypes, n=6 for heterozygotes, n=5 for mutants). Serum aldosterone levels (FIG. 3B) were determined in trunk blood samples from 7–8 month old mice (n=1 for wildtypes, n=2 for heterozygotes, n=3 for mutants). Plasma catecholamine levels (FIGS. 3C–3E) were determined in trunk blood samples from 7–8 month old mice (n=4 for wildtype mice, n=3 for mutant mice).

FIG. 1C shows an RIA analysis of serum ACTH levels in $F_2$ male littermates (measurements in triplicates, one mouse per genotype). Blood was collected retroorbitally and serum was analyzed by RIA following the provider's instructions (ICN, corticosterone; IncStar, ACTH; Linco, Leptin). FIG. 1C shows that ACTH levels in the mutant animal were below the sensitivity of the assay, indicating that the coding region for all Pomc peptides had been deleted.

Serum corticosterone and aldosterone levels were below detection (FIGS. 3A and 3B), despite considerable stressing of mice during blood collection, indicating an absolute necessity for POMC derived peptides for adrenal cortical function. Here again, heterozygotes show a gene dosage effect, suggesting fine-tuned regulation by Pomc peptides. When plasma catecholamine basal levels were measured (FIGS. 3C–3E), epinephrine was significantly lower in Pomc mutants versus wildtype mice (FIG. 3C; p<0.006), while levels of norepinephrine were not significantly altered (FIG. 3D; p<0.27) and dopamine levels were slightly increased in mutants compared to wildtypes (FIG. 3E; p<0.06). In cases of dysfunction of the adrenal medulla, other chromaffin tissues expressing catecholamines increase production to compensate; epinephrine, however, is almost exclusively produced by the adrenal medulla. The significant decrease of epinephrine indicates a severe dysfunction and/or lack of the adrenal medulla in POMC deficient mice. Finding adrenal glands proved to be impossible: mutant mice had no macroscopically discernible adrenal glands. For histological analysis, tissues from the fat pad surrounding the kidney were collected and immediately placed into formalin. Sectioning (5 μm thickness) and staining were carried out by American Histolab, Inc., Gaithersburg, Md. Histological examination of the fat pad surrounding the kidney and presumably containing adrenal tissue revealed areas of tissue reminiscent of rudimentary adrenal medulla or adrenal cortex (data not shown). However, immunohistochemical staining with antibodies against key enzymes in catecholamine synthesis (PNMT and TH) were negative (data not shown).

The lack of a normal adrenal gland structure in POMC null mice points to a critical role of POMC derived peptide (s) in adrenal development. POMC adrenocorticotropin (ACTH) of pituitary origin is the only known ligand for the MC2-R in the adrenal gland. It is surprising that loss of ligand (ACTH) results in loss of the tissue expressing its receptor (MC2-R). Without being bound by theory, the present inventors believe that it may be more likely that another POMC factor distinct from ACTH plays a role as trophic factor in adrenal gland development. Candidate peptides would be peptides derived from the N-terminal non-γ-MSH region of POMC (N-POMC$_{1-28}$, N-POMC$_{2-59}$), which have been implicated in the physiological control of adrenal growth (Estivariz et al., 1982, Nature 297:419–422). This can be tested by reconstituting the POMC null mice with candidate peptides. It may also be possible at that point to determine whether the lack of adrenal medulla is a consequence of the lack of Pomc peptides, or of adrenal cortical structure, or of adrenal cortical factors (i.e., corticosterone).

The phenotype of obesity, adrenal insufficiency, and altered pigmentation, makes the POMC null mouse a model for the human POMC null syndrome. In the human POMC deficient patients and in the mouse Pomc mutant, homozygotes are born within the normal range of weight and size. Development of obesity starts at 4 to 5 months in the reported cases in humans (Krude et al., 1998, Nat. Genet. 19:155–157), and at 1 month in POMC null mice. This time course of obesity is also similar to that seen in fat/fat mice, which lack carboxypeptidase E, a prohormone processing enzyme (Naggert et al., 1995, Nat. Genet. 10:135–142). A defect in processing of POMC could explain the obesity component of the fat/fat phenotype.

In the human POMC deficient patients, ACTH deficiency results in hypocortisolism and, if untreated, in death. In the POMC null mice, the present inventors were unable to detect corticosterone in serum, even under moderate stress conditions. In contrast to humans, mice that develop with maternal but without endogenous corticosterone are viable. A similar observation has been made in mice lacking corticotropin releasing factor, CRH, which develop normally despite very low levels of corticosterone (Muglia et al., 1995, Nature 373:427–432). As in offspring from CRH null females, homozygous offspring from POMC null mutants die within the first hours after birth. This is probably due to defective lung maturation with the lack of corticosterone, as has been demonstrated for the CRH null mutants.

Corticosteroids are known to increase food intake (Tempel et al., 1994, J. Neuroendocrinol. 6:479–501) and to decrease energy expenditure (Strack et al., 1995, Am. J. Physiol. 268:R1209–1206). POMC null mice have no detectable corticosterone, yet they are obese. This is so far the only situation where obesity occurs in the absence of corticosterone. In all other forms of murine obesity, corticosterone is at normal or elevated levels. In fact, the excessive obesity in leptin-deficient mice is largely due to the hypercortisolism in this mouse and adrenalectomy blocks the development of excessive obesity in lep$^{ob}$/lep$^{ob}$ mice (Solomon et al., 1973, Endocrinology 93:510–512 and Tokuyama et al., 1989, Am. J. Physiol. 257:E139–144).

Lack of ligands for the melanocortin receptors in POMC-deficient mice replicate fully or partly the effects seen in mice lacking the receptors MC4-R or MC1-R, respectively. In a preliminary analysis, POMC-deficient mice also replicate the defective water repulsion and thermoregulation seen in mutant mice lacking MC5-R (data not shown). The present results provide a strong indication that Pomc peptides are the physiological ligands for at least some MC5-R mediated functions.

Example 2

The following example demonstrates that administration of a Pomc peptide analog to a mouse having obesity resulted in significant weight loss.

To initially test for the effect of peripheral melanocortins on weight change, we selected the stable agonist [Ac-Cys$^4$, D-Phe$^7$, Cys$^{10}$] αMSH (4–13)(described in Cody et al., 1985, J. Med. Chem. 28, 583–588; incorporated herein by reference in its entirety). Briefly, [Ac-Cys$^4$,D-Phe$^7$, Cys$^{10}$] α-MSH (4–13) amide was obtained from Peninsula Laboratories, CA. Lyophilized powder was dissolved in water at 1 mg/ml, which was diluted in PBS to 10 μg/mL. During the experiments, mice were maintained on a normal 12h/12h light/dark cycle with food and water ad libitum. Mice were fed standard laboratory rodent diet (#5001).

Figures 4A, 4B:
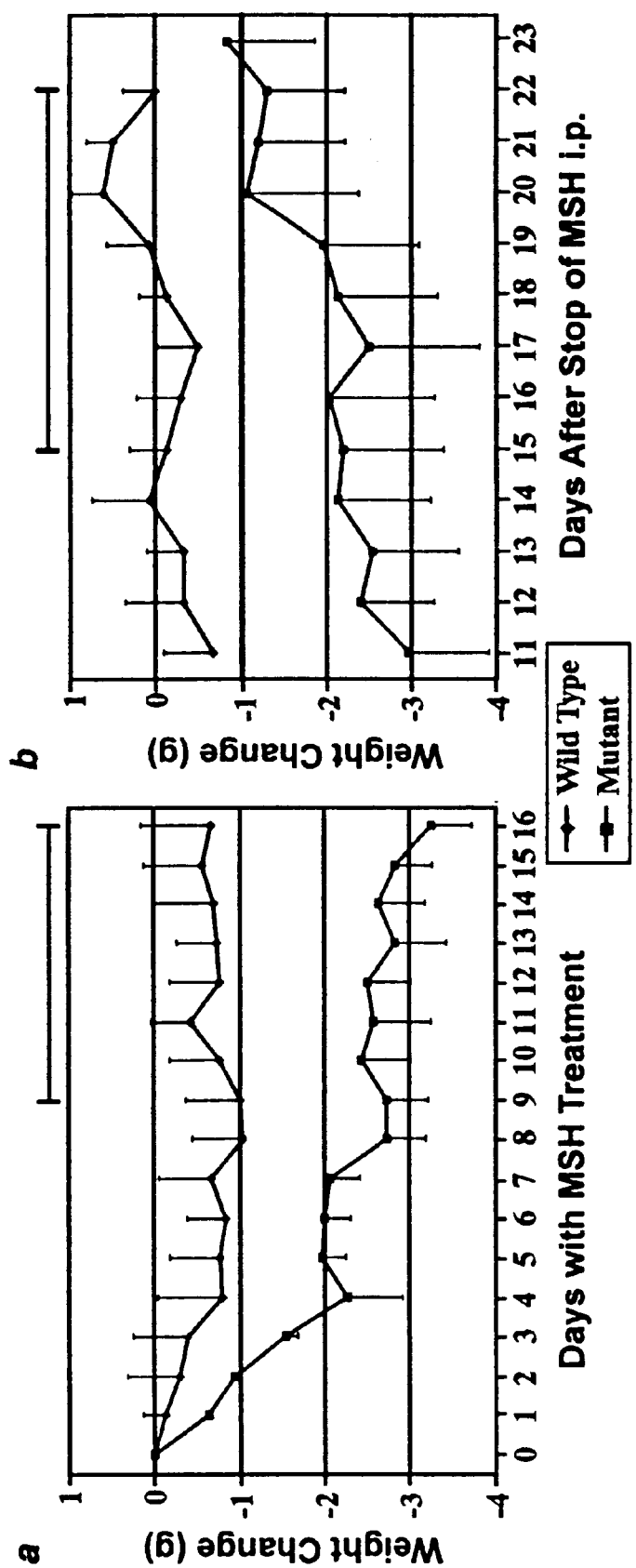
FIG. 4A is a line graph showing the change in body weight from the pretreatment weight for POMC homozygous mutant and wildtype female mice treated with an α-MSH analog once a day.
FIG. 4B is a line graph showing the change in body weight for days 11 to 23 after termination of α-MSH analog treatment.

Daily intraperitoneal injections of one microgram (~1 nmol) of this MSH-agonist (0.1 ml in PBS delivered one to two hours before the onset of darkness) led to a significant weight loss (38% of excess weight within one week, and 46% of excess weight by 2 weeks) in mutant female mice (p<0.1 at day 8, p<0.05 at day 16), but caused no significant weight loss in wildtype littermates (FIG. 4A). FIG. 4A shows the mean change in body weight from the pretreatment weight in grams for groups of three mice (POMC homozygous mutant and wildtype female mice) for the 16-day period of treatment. When the MSH injections were stopped, mutant mice started to gain weight after about 10 days, and reached close to their pretreatment weight after another two weeks (FIG. 4B).

Figure 4D:
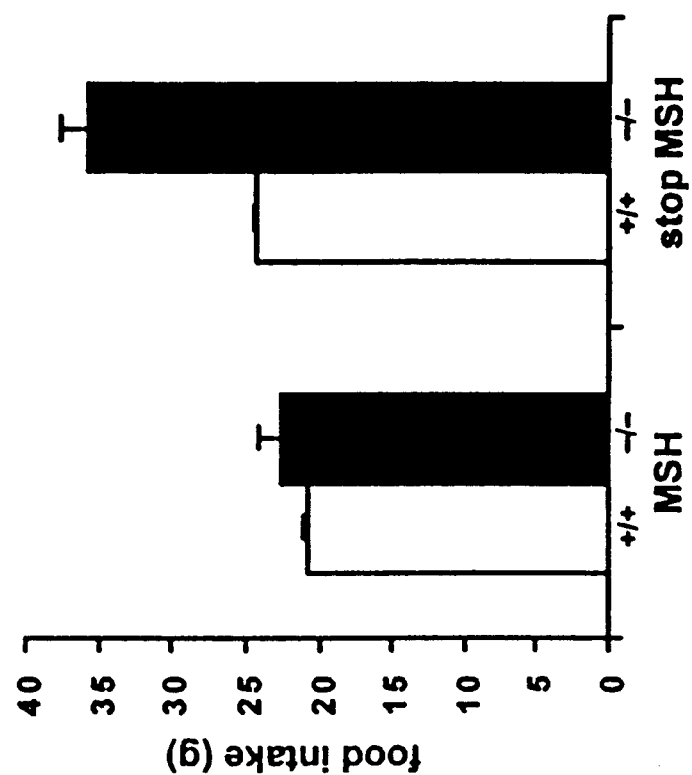
FIG. 4D is a bar graph illustrating the food intake over the second week of MSH treatment as compared to over the third week after termination of treatment for POMC homozygous mutant and wildtype female mice treated with an α-MSH analog once a day.
Figure 4C:
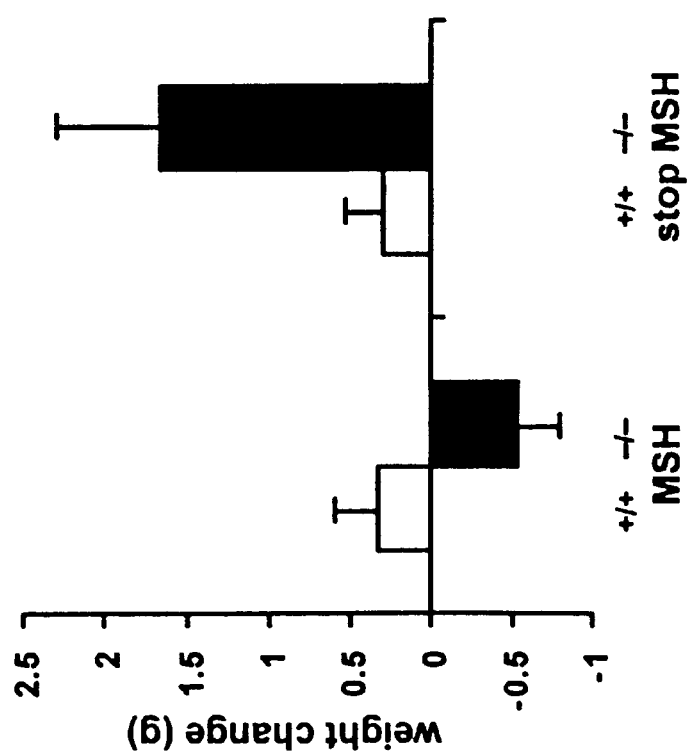
FIG. 4C is a bar graph illustrating the change in body weight over the second week of MSH treatment as compared to over the third week after termination of treatment for POMC homozygous mutant and wildtype female mice treated with an α-MSH analog once a day.

In order to see whether the α-MSH analog has an effect on food intake, we compared weight change and food intake in these mice for one week (see bars in FIGS. 4A and 4B) under MSH analog treatment and after MSH analog treatment was stopped (FIGS. 4C and 4D). During one week under MSH analog treatment mutant mice lost 0.5 g, while wildtype littermates gained 0.3 g; the food intake during this time was equivalent in both groups (20.7 g in wildtypes, and 22.7 g in mutants). After MSH analog treatment had been stopped for two weeks, mutant mice now gained 1.7 g in one week, while wildtype littermates kept their overall weight gain of 0.3 g; food intake now differed significantly between the two groups, with mutants taking up 11.5 g more than wildtypes (35.7 g versus 24.2 g; p<0.005). These results show that lack of αMSH correlates with food intake, although this experiment did not distinguish whether MSH influences body weight primarily through food intake or in combination with a direct effect of melanocortins on adipocytes (inhibition of free fatty acid uptake or stimulation of lipolysis).

An effect of MSH could also be seen on coat pigmentation. The coats of mice treated with MSH for two weeks lost their yellowish tinge (data not shown). Yellow coat pigmentation gradually reappeared after MSH treatment was terminated (data not shown).

Example 3

The following example provides evidence that the major component of weight regulation through the melanocortinergic pathway is not through central, appetite regulating effects.

To further consider the question of central, appetite regulating effects of melanocortins versus peripheral (possibly lipolytic or free fatty acid uptake) effects, weight change and food intake in wildtype and POMC null mutant mice (3 female mice per group) under three experimental conditions were measured (FIGS. 5A–5D): (1) standard mouse diet, no treatment; (2) standard mouse diet, MSH analog intraperitoneally (1 or 2 μg, once daily); and (3) high fat diet (#5020), no treatment. With respect to weight regulation, wildtype mice are completely capable of maintaining their body weight constant under those varying conditions (FIG. 5A). Mutant mice lacking Pomc peptides gain weight with standard diet, lose excess weight when treated with MSH analog peripherally, and gain more than double the weight with high-fat diet as they gain with standard diet (FIG. 5C). Table 1 shows the statistical significance of the comparisons between genotype, diet, and MSH analog treatment with respect to weight change and food intake. P values were determined by ANOVA. If the major component of weight regulation through the melanocortinergic pathway was the regulation of feeding behavior, the observed changes in body weight in POMC null mutant mice should be paralleled by a similar pattern in food uptake. This, however, was not observed (FIGS. 5B and 5D and Table 1). Rather, the following observations were made: (1) compared to wild-type mice when fed a standard diet, Pomc mutant mice are hyperphagic, and they gain weight, yet with MSH analog treatment, they lose weight despite still being hyperphagic; (2) MSH analog treatment decreases food intake in both wildtype and mutant mice, yet only mutant mice lose significant weight; (3) when fed a high fat diet, food intake is unchanged in mutant and wildtype mice compared to feeding on standard diet, as well as compared between mutant and wildtype mice, yet mutant mice gain significant weight, both compared to standard diet and compared to wildtype mice.

TABLE 1

| Com-parisons | | weight change | P value | food intake | P value |
|---|---|---|---|---|---|
| wildtype mice | standard diet v. standard diet & MSH analog treatment | ←→ | >0.05 | ↓ | <0.05 |
| | standard diet v. high fat diet | ←→ | >0.05 | ←→ | >0.05 |
| mutant mice | standard diet v. standard diet & MSH analog treatment | ↓ | <0.005 | ↓ | <0.05 |
| | standard diet v. high fat diet | ↑ | <0.05 | ←→ | >0.05 |
| standard diet | wildtype v. mutant | ↑ | <0.05 | ↑ | <0.05 |
| standard diet & MSH analog treatment | wildtype v. mutant | ↓ | <0.05 | ↑ | <0.05 |
| high fat diet | wildtype v. mutant | ↑ | <0.0005 | ←→ | >0.05 |

In experiments assaying transient regulation of feeding behavior, 3 nmol MSH agonist were needed to see a significant effect on food intake when applied intracerebroventricularly; and 100 nmol of agonist were needed when administered intraperitoneally (Kastin et al., ibid.). This is 100 times more than was applied in the present experiments, assaying weight change. Furthermore, the level of MSH agonist that was given peripherally in these experiments is approximately that of the endogenous melanocortin in a normal mouse.

The weight losses and gains of Pomc mutant mice in the present experiments cannot be explained solely by their feeding behavior. Rather, these data are consistent with both central and peripheral actions of melanocortins. POMC-deficient mice show both increased food intake and disregulation of metabolism (fat storage/release). Treatment with peripheral melanocortin agonist results in significant weight loss in mutant obese, but not in wildtype, non-obese mice. This may be either a direct effect of melanocortins on adipocytes (inhibition of free fatty acid uptake and/or stimulation of lipolysis) or an indirect effect mediated by another mechanism.

The adult-onset obesity resulting from overexpression of agouti signaling protein in $A^y$ mice (Lu et al., ibid.), or from overexpression of agouti related protein (AGRT or agouti related transcript, ART) in transgenic mice (Graham et al., ibid. and Ollmann et al., ibid.), are generally interpreted as consequences of antagonism of α-MSH on hypothalamic MC4-R. However, without being bound by theory, the present inventors believe that the competition for binding sites with oα-MSH may also be in the periphery, given the present results taken together with data which shows that agouti stimulates adipogenesis (Jones et al., 1996, *Am. J. Physiol.* 270:E192–196) and antagonizes melanocortin-mediated lipolysis (Xue et al., 1998, *Faseb J.* 12:1391–1396) directly in adipocytes. Another observation underlying the importance of peripheral mechanisms of weight regulation is that of leptin treatment in the obese mouse, which leads to a loss in body weight not accounted for by a simple decrease of food intake (Levin et al., 1996, *Proc. Natl. Acad. Sci. USA* 93:1726–1730). The lipolytic effects of melanocortins in rabbits have been described (Kastin et al., 1975, *Pharmacol. Biochem. Behav.* 3:121–126 and Richter et al., 1987, *Neuropeptides* 9:59–74). Melanocortins circulate in the periphery and their receptors are found in peripheral tissues; specifically, melanocortin receptors are found on adipocytes (Boston et al., 1996, *Endocrinology* 137:2043–2050).

While various embodiments of the present invention have been described in detail, it is apparent that modifications and adaptations of those embodiments will occur to those skilled in the art. It is to be expressly understood, however, that such modifications and adaptations are within the scope of the present invention.

What is claimed is:

1. A genetically modified mouse useful for studying peripheral and central pathways of energy homeostasis, said genetically modified mouse comprising a genetic modification within two alleles of its Pomc locus, the genetic modification comprising a deletion, a substitution, or a modification of exon 3 of the Pomc locus or a deletion, a substitution, or a modification preventing or reducing expression of exon 3 of the Pomc locus, wherein said genetic modification results in an absence of proopiomelanocortin (Pomc) peptide action in said mouse and further wherein the genetic modification results in the mouse having obesity and showing a loss in body weight when treated peripherally with a stable MSH agonist.

2. The genetically modified mouse of claim 1, wherein said genetic modification is a modification in a nucleic acid sequence comprising exon 3 of said Pomc locus, wherein said modification results in an absence of proopiomelanocortin (Pomc) peptide action in said mouse.

3. The genetically modified mouse of claim 1, wherein said genetic modification is a modification within a region of said Pomc locus other than exon 3, wherein said modification results in an absence of proopiomelanocortin (Pomc) peptide action in said mouse.

4. The genetically modified mouse of claim 3, wherein said region of said Pomc locus other than exon 3 is selected from the group consisting of exon 1, exon 2 and a regulatory region of said Pomc locus.

5. The genetically modified mouse of claim 1, wherein said genetic modification is selected from the group consisting of a deletion, an insertion, a substitution and an inversion of nucleotides in said Pomc locus.

6. The genetically modified mouse of claim 1, wherein said genetic modification is a deletion of a nucleic acid sequence within two alleles of said Pomc locus, wherein said deletion results in an absence of expression of Pomc peptides by said mouse.

7. The genetically modified mouse of claim 1, wherein said genetic modification is a deletion of a nucleic acid sequence comprising exon 3 of Pomc.

8. The genetically modified mouse of claim 1, wherein said genetic modification is a deletion of exon 3 of Pomc.

9. The genetically modified mouse of claim 1, wherein said genetic modification is a deletion of a portion of exon 3 of Pomc sufficient to prevent expression of Pomc peptides by two alleles in said genome.

10. The genetically modified mouse of claim 1, wherein said genetic modification is a deletion from said genome of a nucleic acid sequence comprising SEQ ID NO:7.

11. The genetically modified mouse of claim 1, wherein said mouse is also characterized by a phenotype selected from the group consisting of a defect in adrenal development and altered pigmentation.

12. The genetically modified mouse of claim 1, wherein said mouse has measurably increased serum leptin levels as compared to a wild-type sibling of said mouse.

13. The genetically modified mouse of claim 1, wherein said mouse has an increased food uptake as compared to a wild-type sibling of said mouse.

14. The genetically modified mouse of claim 1, wherein said mouse has measurably reduced serum levels of a hormone selected from the group consisting of corticosterone, aldosterone and epinephrine as compared to a wild-type sibling of said mouse.

15. The genetically modified mouse of claim 1, wherein said absence of proopiomelanocortin (Pomc) peptide action is an absence of melanocyte stimulating hormone (MSH) action.

16. The genetically modified mouse of claim 15, wherein said genetic modification is modification in a nucleic acid sequence comprising exon 3 of said Pomc lows.

17. The genetically modified mouse of claim 15, wherein said genetic modification is a modification within a regulatory region of said Pomc locus.

18. The genetically modified mouse of claim 15, wherein said genetic modification is selected from the group consisting of a deletion, an insertion, a substitution and an inversion of nucleotides in mid Pomc locus.

19. The genetically modified mouse of claim 15, wherein said genetic modification is a deletion of a nucleic acid sequence within two alleles of said Pomc locus.

20. The genetically modified mouse of claim 15, wherein said genetic modification is a deletion of exon 3 of Pomc.

21. The genetically modified mouse of claim 15, wherein said genetic modification is a deletion of a portion of exon 3 of Pomc sufficient to prevent expression of MSH by two alleles in said genome.

22. The genetically modified mouse of claim 15, wherein said mouse has measurably increased serum leptin levels as compared to a wild-type sibling of said mouse.

23. The genetically modified mouse of claim 15, wherein said mouse has an increased food uptake as compared to a wild-type sibling of said mouse.

24. A method for studying the molecular and biochemical events associated with obesity, comprising:
  a. harvesting cells, tissues or body fluids from a genetically modified mouse comprising a genetic modification within two alleles of its Pomc locus, the genetic modification comprising a deletion, a substitution, or a modification of exon 3 of the Pomc locus or a deletion, a substitution, or a modification of another region of the Pomc locus preventing or reducing expression of exon 3 of the Pomc locus, wherein said genetic modification results in an absence of proopiomelanocortin (Pomc) peptide action in said mouse and further wherein the genetic modification results in the mouse having obesity and showing a loss in body weight when treated peripherally with a stable MSH agonist; and,
  b. comparing said cells, tissues or body fluids from said genetically modified mouse to cells, tissues or body fluids from a wild-type sibling of said genetically modified mouse.

25. The method of claim 24, wherein said step of comparing is performed by an assay selected from the group consisting of morphological examination of said cells, tissues or body fluids; histological examination of said cells, tissues or body fluids; evaluation of Pomc peptide biological activity in said mouse; evaluation of free fatty acid metabolism in said mouse; evaluation of lipolysis and fatty acid sequestration in said mouse; evaluation of weight gain or loss in said mouse; evaluation of hormone levels in said mouse; and, evaluation of blood biochemistry in said mouse.

26. The method of claim 24, wherein said absence of proopiomelanocortin (Pomc) peptide action is an absence of MSH peptide action.

27. A method to identify compounds useful in regulating peripheral and central pathways of energy homeostasis, comprising:
  a. administering a compound to be evaluated to a genetically modified mouse comprising a genetic modification within two alleles of its Pomc locus, the genetic modification comprising a deletion, a substitution, or a modification of exon 3 of the Pomc locus or a deletion, a substitution, or a modification of another region of the Pomc locus preventing or reducing expression of exon 3 of the Pomc locus, wherein said genetic modification results in an absence of proopiomelanocortin (Pomc) peptide action in said mouse and further wherein the genetic modification results in the mouse having obesity and showing a loss in body weight when treated peripherally with a stable MSH agonist; and,
  b. evaluating physiological changes in said genetically modified mouse as compared to a mouse selected from the group consisting of (a) a second genetically modified mouse comprising a genetic modification within at least one allele of its Pomc locus, wherein said genetic modification results in a reduction in proopiomelanocortin (Pomc) peptide action in said mouse; and (b) a third mouse having a genome comprising a wild-type Pomc locus at two alleles.

28. The method of claim 27, wherein said compound is a proopiomelanocortin (Pomc) analog.

29. The method of claim 27, wherein said compound is selected from the group consisting of a melanocortin analog and lipocortin analog.

30. The method of claim 27, wherein said compound is a melanocortin analog.

31. The method of claim 27, wherein said compound is selected from the group consisting of a homologue of MSH, a peptide mimetic of MSH, and a non-peptide mimetic of MSH.

32. The method of claim 27, wherein said compound is a peptide mimetic of MSH.

33. The method of claim 27, wherein said compound is an analog of a peptide having an amino acid sequence represented herein by SEQ ID NO: 1.

34. The method of claim 27, wherein said compound is an α-MSH analog selected from the group consisting of:
  a. [Ac-Cys$^4$, D-Phe$^7$, Cys$^{10}$] α-MSH;
  b. Ac-[Nle$^4$, X$_{aa}^5$, His$^6$, X$_{aa}^7$, Arg$^7$, Trp$^9$, X$_{aa}^{10}$]-NH$_2$, (SEQ ID NO:3)
    wherein X$_{aa}^5$ is Glu or Asp, X$_{aa}^7$ is Phe or D-Phe and X$_{aa}^{10}$ is a dibasic amino acid; Lys; ornithine; 2,4,-diaminobutyric acid; or 2,3 diaminopropionic acid (Dpr);
  c. AC-[Cys$^4$, Cys$^{10}$] α-MSH$_{1-13}$NH$_2$;
  d. R$_1$-W-X-Y-Z-R$_2$,
    wherein R$_1$ is selected from the group consisting of Ac-Gly-, Ac-Met-Glu-, Ac-Nle-Glu- and Ac-Tyr-Glu-;
    W is selected from the group consisting of -His- and -D-His-;
    X is selected from the group consisting of -Phe-, -D-Phe-, -Tyr, -D-Tyr-, (-pNO$_2$)D-Phe$^7$-;
    Y is selected from the group consisting of -Arg- and -D-Arg-;
    Z is selected from the group consisting of -Trp- and -D-Trp-; and,
    RZ is selected from the group consisting of -NH$_2$, -Gly-NH$_2$, and -Gly-Lys-NH$_2$;
  e. Ac-Ser-Tyr-Ser-Xaa-Glu-His-D-Phe-Arg-Trp-Gly-Lys-Pro-Val-NH$_2$ (SEQ ID NO:4), wherein Xaa is selected from the group consisting of Met, Nle, and Cys;

f. [Nle⁴, D-Phe⁷]-α-MSH;

g. [Nle⁴, D-Phe⁷]-α-MSH$_{4-10}$;

h. [Nle⁴, D-Phe⁷]-α-MSH$_{4-11}$;

i. [Nle⁴, D-Phe⁷, D-Trp⁹]-α-MSH$_{4-11}$;

j. [Nle⁴, D-Phe⁷]-α-MSH$_{4-9}$;

k. Ac-[Nle⁴, AA⁵, D-Phe⁷, AA¹⁰]-R$_1$ or Ac-[Nle⁴, AA⁵, D-Phe⁷, AA¹¹]-R$_2$;

wherein AA⁵ may be either a L- or D- amino acid having an omega amino or carboxyl group in the side chain selected from the group consisting of α, γ-diaminopropionic acid; α, γ-diaminobutyric acid, Orn, Lys, α,β-aminoadipic acid, α-aminopimelic acid, Glu or Asp;

wherein AA¹⁰ may be diaminopropionic acid, α, γ-diaminobutyric acid, Orn, Lys, α,β-aminoadipic acid, α-aminopimelic acid, Glu or Asp;

wherein R$_1$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$;

wherein AA¹¹ may be L- or D- amino acid having an omega-amino or carboxyl group in the side chain selected from the group consisting of α,β-diaminopropionic acid; α,γ-diaminobutyric acid, Orn, Lys, α-aminoadipic acid, α-aminopimelic acid, Glu or Asp;

wherein R$_2$ is the designation α-MSH$_{1-13}$NH$_2$, α-MSH$_{1-12}$NH$_2$, α-MSH$_{1-11}$NH$_2$, α-MSH$_{4-13}$NH$_2$; and, wherein Xxx may be from 1 to 5 α-amino acid residues each of which may be of L- or D- configuration, or a linear or branched chain spacer;

l.

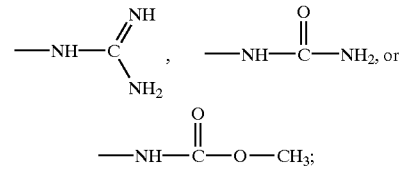

Ac—Nle-Asp-His-D-Nal-Arg-Trp-Lys-NH$_2$; and (SEQ ID NO: 5)

m.

Ac—Nle-Asp-His-D-p-l-Phe-Arg-Trp-Lys-NH$_2$; and, (SEQ ID NO: 6)

n.

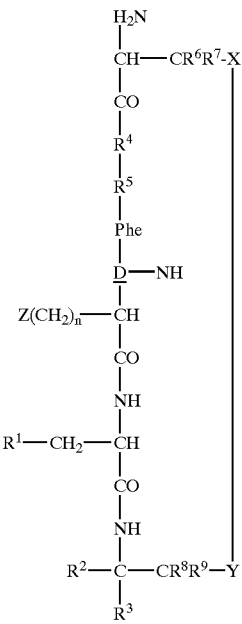

wherein R¹ is a substituted or unsubstituted aromatic radical;
R² is hydrogen or a methyl group;
R³ is a carboxylate, carboxamide, hydroxymethyl, or aldehyde group;
R⁴ is glutamic acid, alanine, -amino butyric acid, valine, leucine or isoleucine;
R⁵ is histidine, glutamic acid, alanine, valine, leucine or isoleucine;
R⁶ and R⁷, which may be the same or different, are hydrogen, methyl or lower alkyl having one to five carbon atoms;
R⁸ and R⁹, which may be the same or different, are hydrogen, methyl or lower alkyl having one to five carbon atoms;
X and Y are sulfur, methylene, SO or SO$_2$;
Z is -NH$_2$, $$-NH-C\overset{NH}{\underset{NH_2}{\diagdown}}, \quad -NH-\overset{O}{\underset{\|}{C}}-NH_2, \text{ or}$$

$$-NH-\overset{O}{\underset{\|}{C}}-O-CH_3;$$

and,
n is an integer greater than or equal to 2;

o.

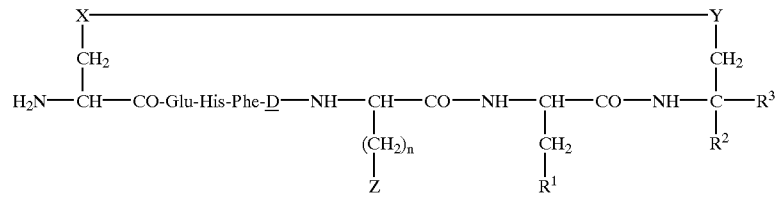

wherein $R^1$ is phenyl, indole, p-hydroxyphenyl, p-aminophenyl, imidazole, l-naphthyl adamantyl or alkylphenyl, 2-naphthyl;

$R^2$ is hydrogen or a methyl group;

$R^3$ is a carboxylate, carboxamide, hydroxymethyl, or aldehyde group;

X and Y are sulfur, methylene, SO or $SO_2$;

Z is $-NH_2$,

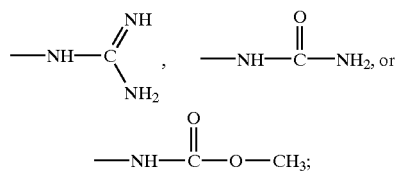

and, n is an integer greater than or equal to 2; and wherein the cyclized portion of the compound is conformationally restricted in a manner which is compatible with the reactivity of the compound with receptors of the central nervous system.

35. The method of claim 27, wherein said compound is a peptide comprising an amino acid sequence represented by SEQ ID NO:1.

36. The method of claim 27, wherein said absence of proopiomelanocortin (Pomc) peptide action is an absence of MSH peptide action and said reduction of proopiomelanocortin (Pomc) peptide action is a reduction in MSH peptide action.

37. The method of claim 36, wherein said compound is a melanocortin analog.

38. The method of claim 36, wherein said compound is selected from the group consisting of a homologue of MSH, a peptide mimetic of MSH, and a non-peptide mimetic of MSH.

39. The method of claim 36, wherein said compound is a peptide mimetic of MSH.

40. The method of claim 36, wherein said compound is an analog of a peptide having an amino acid sequence represented herein by SEQ ID NO: 1.

41. The method of claim 36, wherein said compound is an α-MSH analog selected from the group consisting of:

a. [Ac-$Cys^4$, D-$Phe^7$, $Cys^{10}$] α-MSH;

b. Ac-[$Nle^4$, $X_{aa}^5$, $His^6$, $Arg^7$, $Trp^9$, $X_{aa}^{10}$]-$NH_2$, (SEQ ID NO:3)
wherein $X_{aa}^5$ is Glu or Asp, $X_{aa}^7$ is Phe or D-Phe and $X_{aa}^{10}$ is a dibasic amino acid; Lys; ornithine; 2,4-diaminobutyric acid; or 2,3 diaminopropionic acid (Dpr):

c. Ac-[$Cys^4$, $Cys^{10}$] α-$MSH_{1-13}NH_2$;

d. $R_1$-W-X-Y-Z-$R_2$,
wherein $R_1$ is selected from the group consisting of Ac-Gly-, Ac-Met-Glu-, Ac-Nle-Glu- and Ac-Tyr-Glu-;

W is selected from the group consisting -His- and -D-His-;

X is selected from the group consisting of -Phe-, -D-Phe-, -Tyr, -D-Tyr-, (-$pNO_2$)D-$Phe^7$-:

Y is selected from the group consisting of -Arg- and -D-Arg-;

Z is selected from the group consisting of -Trp- and -D-Trp-; and,

RZ is selected from the group consisting of -$NH_2$, -Gly-$NH_2$, and -Gly-Lys-$NH_2$:

e. Ac-Ser-Tyr-Ser-Xaa-Glu-His-D-Phe-Arg-Trp-Gly-Lys-Pro-Val-$NH_2$ (SEQ ID NO:4), wherein Xaa is selected from the group consisting of Met, Nle, and Cys;

f. [$Nle^4$, D-$Phe^7$]-α-MSH:

g. [$Nle^4$, D-$Phe^7$]-α-$MSH_{4-10}$;

h. [$Nle^4$, D-$Phe^7$]-α-$MSH_{4-11}$;

i. [$Nle^4$, D-$Phe^7$, D-$Trp^9$]-α-$MSH_{4-11}$;

j. [$Nle^4$, D-$Phe^7$]-α-$MSH_{4-9}$;

k. Ac-[$Nle^4$, $AA^5$, D-$Phe_7$, $AA^{10}$]-$R_1$ or Ac-[$Nle^4$, $AA^5$, D-$Phe_7$, $AA^{11}$]-$R_2$;

wherein $AA^5$ may be either a L- or D- amino acid having an omega amino or carboxyl group in the side chain, selected from the group consisting of α,γ-diaminopropionic acid; α,γ-diaminobutyric acid, Orn, Lys, α,β-aminoadipic acid, α-aminopimelic acid, Glu or Asp;

wherein $AA^{10}$ may be diaminopropionic acid, α,γ-diaminobutyric acid, Orn, Lys, α,β-aminoadipic acid, α-aminopimelic acid, Glu or Asp; wherein $R_1$ is the designation α-$MSH_{1-13}NH_2$, α-$MSH_{1-12}NH_2$, α-$MSH_{1-11}NH_2$, α-$MSH_{4-13}NH_2$, or α-$MSH_{4-10}NH_2$;

wherein $AA^{11}$ may be L- or D-amino acid having omega-amino or carboxyl group in the side chain, selected from the group consisting of α,γ-diaminopropionic acid; α,γ-diaminobutyric acid, Orn, Lys, α-aminoadipic acid, α-aminopimelic acid, Glu or Asp;

wherein $R_2$ is the designation α-$MSH_{1-13}NH_2$, α-$MSH_{1-12}NH_2$, α-$MSH_{1-11}NH_2$, α-$MSH_{4-13}NH_2$; and, wherein Xxx may be from 1 to 5 a-amino acid residues each of which may be of L- or D- configuration, or a linear or branched chain spacer;

l.

Ac—Nle-Asp-His-D-Nal-Arg-Trp-Lys-$NH_2$; and (SEQ ID NO: 5)

m.

Ac—Nle-Asp-His-D-p-l-Phe-Arg-Trp-Lys-$NH_2$; and, (SEQ ID NO: 6)

n.

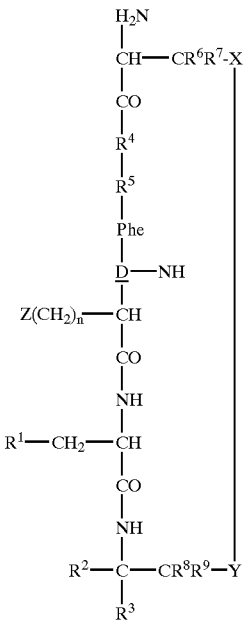

wherein $R^1$ is a substituted or unsubstituted aromatic radical;

$R^2$ is hydrogen or a methyl group;

$R^3$ is a carboxylate, carboxamide, hydroxymethyl, or aldehyde group;

$R^4$ is glutamic acid, alanine, -amino butyric acid, valine, leucine or isoleucine;

$R^5$ is histidine, glutamic acid, alanine, valine, leucine or isoleucine;

$R^6$ and $R^7$, which may be the same or different, are hydrogen, methyl or lower alkyl having one to five carbon atoms, $R^8$ and $R^9$, which may be the same or different, are hydrogen, methyl or lower alkyl having one to five carbon atoms;

X and Y are sulfur, methylene, SO or $SO_2$;

Z is $-NH_2$,

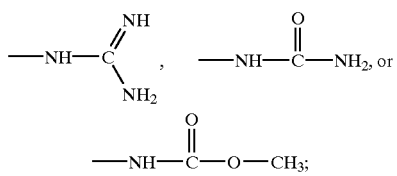

and, n is an integer greater than or equal to 2;

o.

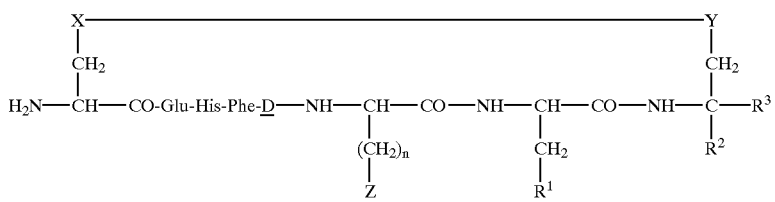

wherein $R^1$ is phenyl, indole, p-hydroxyphenyl, p-aminophenyl, imidazole, I-naphthyl adamantyl or alkylphenyl, 2-naphthyl;

$R^2$ is hydrogen or a methyl group;

$R^3$ a carboxylate, carboxamide, hydroxymethyl, or aldehyde group;

X and Y are sulfur, methylene, SO or $SO_2$;

Z is $-NH_2$,

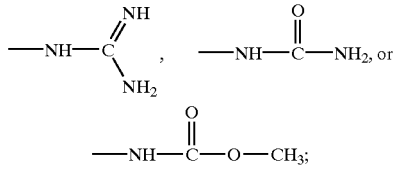

and, n is an integer greater than or equal to 2; and wherein the cyclized portion of the compound is conformationally restricted in a manner which is compatible with the reactivity of the compound with receptors of the central nervous system.

42. The method of claim 36, wherein said compound is a peptide comprising an amino acid sequence represented by SEQ ID NO:1.

43. A method of producing a genetically modified mouse useful for studying peripheral and central pathways of energy homeostasis, comprising:

a. introducing into an embryonic stem cell of a mouse a targeting vector comprising a Pomc locus containing a modification of a nucleic acid sequence sufficient to result in a reduction in proopiomelanocortin (Pomc) peptide action in said mouse, the modification comprising a deletion, a substitution, or a modification of exon 3 of the Pomc locus or a deletion, a substitution, or a modification preventing or reducing expression of exon 3 of the Pomc locus; and, b. obtaining progeny having two alleles containing said modification stably incorporated into their genome, wherein said modification of said nucleic acid sequence results in an absence of expression of proopiomelanocortin (Pomc) peptides by said mouse and further wherein the genetic modification results in the mouse having obesity and showing a loss in body weight when treated peripherally with a stable MSH agonist.

44. The method of claim 43, wherein said reduction of proopiomelanocortin (Pomc) peptide action is a absence of MSH peptide action and further wherein said reduction in expression of proopiomelanocortin (Pomc) peptides is an absence of expression of MSH peptides.

45. The method of claim 43, wherein said absence of expression of proopiomelanocortin (Pomc) peptides is an absence of expression of MSH peptides.

46. A genetically modified mouse useful for studying peripheral and central pathways of energy homeostasis, wherein said genetically modified mouse is produced by a method comprising the steps of:

a. isolating from a source of murine genomic DNA a nucleic acid molecule comprising SEQ ID NO:7;

b. deleting a nucleic acid sequence comprising SEQ ID NO:7 from said nucleic acid molecule to form a genetically modified nucleic acid molecule;

c. inserting a selectable marker into said genetically modified nucleic acid molecule to create a targeting vector, d. transfecting said targeting vector into embryonic stem cells;

e. selecting embryonic stem cells from step (d) which have incorporated said targeting vector at a target locus comprising SEQ ID NO:7 by homologous recombination;

f. inserting said embryonic stem cells selected in step (e) into non-human animal blastocysts;

g. impregnating a female surrogate with said non-human animal blastocysts to produce said genetically modified mouse, wherein the genetic modification results in the mouse having obesity and showing a loss in body weight when treated peripherally with a stable MSH agonist.

* * * * *

UNITED STATES PATENT AND TRADEMARK OFFICE
CERTIFICATE OF CORRECTION

PATENT NO.   : 6,603,058 B1
DATED        : August 5, 2003
INVENTOR(S)  : Miles B. Brennan et al.

It is certified that error appears in the above-identified patent and that said Letters Patent is hereby corrected as shown below:

Title page,
Item [56], References Cited, OTHER PUBLICATIONS, "Eichhom et al.," reference, delete "Eichhom" and substitute -- Eichhorn -- in its place.

Column 39,
Line 14, insert -- a -- before "modification in a nucleic" and
Line 15, delete "lows." and substitute -- locus. -- in its place.
Line 22, delete "mid" and substitute -- said -- in its place.

Column 40,
Line 29, insert -- a -- before "lipocortin".

Column 41,
Line 28, delete "wherein $R_1$".
Line 34, after "or Asp;" insert -- wherein $R_1$ --
Line 53, delete "; and, (SEQ ID NO: 6)" and substitute -- (SEQ ID NO: 6); and -- in its place.

Column 43,
Line 2, delete "I-naphthyl" and substitute -- 1-naphthyl -- in its place.
Line 45, insert -- $X_{aa}^7$, -- after "$His^6$,".
Line 50, immediately after "(Dpr)" delete ":" (colon) and substitute -- ; -- (semicolon) in its place.
Line 58, immediately after "$D-Phe^7$-" delete ":" (colon) and substitute -- ; -- (semicolon) in its place.
Line 64, immediately after "$NH_2$" delete ":" (colon) and substitute -- ; -- (semicolon) in its place.

Column 44,
Line 1, immediately after "MSH" delete ":" (colon) and substitute -- ; -- (semicolon) in its place.
Line 21, delete "α,γ-diaminopropionic" and substitute -- α,β-diaminopropionic -- in its place.
Line 37, delete "; and, (SEQ ID NO: 6)" and substitute -- (SEQ ID NO: 6); and, -- in its place.

UNITED STATES PATENT AND TRADEMARK OFFICE
CERTIFICATE OF CORRECTION

PATENT NO.    : 6,603,058 B1
DATED         : August 5, 2003
INVENTOR(S)   : Miles B. Brennan et al.

It is certified that error appears in the above-identified patent and that said Letters Patent is hereby corrected as shown below:

<u>Column 45,</u>
Line 10, immediately after "carbon atoms" delete "," (comma) and substitute -- ; -- (semicolon) in its place.
Line 42, delete "I-naphthyl" and substitute -- 1-naphthyl -- in its place.
Line 45, insert -- is -- after "$R^3$".

Signed and Sealed this

Twenty-fifth Day of May, 2004

JON W. DUDAS
*Acting Director of the United States Patent and Trademark Office*